(12) United States Patent
Hehenberger et al.

(10) Patent No.: US 6,884,394 B1
(45) Date of Patent: Apr. 26, 2005

(54) CHEMICAL INDICATOR READER

(75) Inventors: Rodney K. Hehenberger, Apple Valley, MN (US); Phillip A. Bolea, White Bear Lake, MN (US); Bernard A. Gonzalez, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/369,410

(22) Filed: Aug. 5, 1999

(51) Int. Cl.$^7$ .............................................. G01N 21/00
(52) U.S. Cl. ......................... 422/55; 422/56; 422/58; 422/82.05; 422/82.09; 436/1; 436/8; 436/164; 436/165; 436/169; 436/172
(58) Field of Search .......................... 422/55, 56, 58, 422/68.1, 82.05, 82.06, 82.08, 82.09, 99; 436/169, 8, 1, 164, 165, 172

(56) References Cited

U.S. PATENT DOCUMENTS

| 3,239,429 A | 3/1966 | Menolassino et al. ........ 195/54 |
| 3,661,717 A | 5/1972 | Nelson ................. 195/103.5 R |
| 3,667,916 A | 6/1972 | Sliva et al. ................ 23/230 R |

(Continued)

FOREIGN PATENT DOCUMENTS

| CA | 1 024 300 | 5/1986 |
| EP | 0 117 390 | 9/1990 |
| EP | 630 820 | 12/1994 |
| EP | 0 914 833 | 5/1999 |
| GB | 2 212 310 | 7/1989 |
| GB | 2 052 731 | 1/1991 |
| WO | WO 94/27144 | 11/1994 |
| WO | 96/33242 | 10/1996 |
| WO | WO98/14777 | 4/1998 |
| WO | WO 98/51816 | 11/1998 |
| WO | 98/58683 | 12/1998 |

OTHER PUBLICATIONS

Good Hospital Practice: Stream Sterilization and Sterility Assurance, AAMI Recommended Practice, Section 6.4 (1988).
Sterilization of Health Care Products—Chemical Indicators—Part 1: General Requirements, ANSI/AAMI ST60–(1966).
ISO 11140–1:1995.
European Standard Nos. EN867–1 and 866–1.
The European Committee for Standardization's European Standard No. EN 867–1, Non–biological systems for use in sterilizers—Part 1: General Requirements.
Addams, et al., Bar Coding: An Effective Productivity Concept, JONA, vol. 21, No. 10 (10/91).
Weilert et al., Putting Bar Codes to Work for Improved Patients Care, Clinics in Laboratory Medicine, vol. 11, No. 1 (3/91).
ANSI/AAMI ST45–1992 Bier/Steam Vessels.
Longe et al., Bar Code Technology in Health Care: A Tool for Enhancing Quality, Productivity, and Cost Management, Advanstar Communication, ISBN 0–929870–20–4, Library of Congress Catalog Card No. 93–71570 (1993).
Chobin, N. G., Cost Analysis of Three Low Temperature Sterilization Systems, Journal of Healthcare Material Management, p. 29, 08/94.
U.S. Appl. No. 09/368,744, filed Aug. 05, 1999, Kirckof et al.

(Continued)

*Primary Examiner*—Jill Warden
*Assistant Examiner*—Dwayne K Handy
(74) *Attorney, Agent, or Firm*—Daniel R. Pastirik

(57) ABSTRACT

A reader for a sterilization indicator having sterilizing agent sensitive indicia is described. The indicator allows a sterilization cycle to be monitored without the need for a user to subjectively distinguish between color, quality or intensity of display patterns.

16 Claims, 25 Drawing Sheets

U.S. PATENT DOCUMENTS

| | | | |
|---|---|---|---|
| 3,684,737 A | | 8/1972 | Emigh .................... 252/408 |
| 3,852,034 A | | 12/1974 | Gunther ................ 23/232 R |
| 3,862,824 A | | 1/1975 | Chapman ............... 23/253 TP |
| 3,907,503 A | | 9/1975 | Betts ..................... 23/253 R |
| 4,015,937 A | | 4/1977 | Miyamoto et al. ........ 23/230 R |
| 4,091,921 A | | 5/1978 | Lewis .................... 206/363 |
| 4,094,642 A | | 6/1978 | Sumimoto et al. ........ 23/254 R |
| 4,098,577 A | | 7/1978 | Halpern .................. 23/232 R |
| 4,115,068 A | | 9/1978 | Joslyn .................... 422/58 |
| 4,145,186 A | | 3/1979 | Andersen ................. 23/232 R |
| 4,382,063 A | | 5/1983 | Romito et al. ............ 422/57 |
| 4,410,493 A | | 10/1983 | Joslyn .................... 422/58 |
| 4,579,715 A | | 4/1986 | Bruso .................... 422/58 |
| 4,594,223 A | | 6/1986 | Dyke et al. .............. 422/56 |
| 4,596,696 A | | 6/1986 | Scoville, Jr. ............. 422/61 |
| 4,636,472 A | | 1/1987 | Bruso .................... 435/287 |
| 4,656,600 A | | 4/1987 | Swann .................... 364/567 |
| 4,657,870 A | * | 4/1987 | Ryder et al. ............. 435/311 |
| 4,681,454 A | | 7/1987 | Breemer ................. 356/402 |
| 4,692,307 A | | 9/1987 | Bruso .................... 422/58 |
| 4,696,580 A | | 9/1987 | Kameda ................. 374/162 |
| 4,699,765 A | | 10/1987 | Hambleton .............. 422/57 |
| 4,756,758 A | | 7/1988 | Lent et al. |
| 4,850,716 A | | 7/1989 | Baker et al. ............. 374/160 |
| 4,855,909 A | | 8/1989 | Vincent et al. |
| 4,877,745 A | | 10/1989 | Hayes et al. |
| 4,898,762 A | | 2/1990 | Brown et al. ............ 428/152 |
| 4,935,371 A | | 6/1990 | Rickloff ................. 435/296 |
| 4,943,939 A | | 7/1990 | Hoover .................. 364/555 |
| 5,063,297 A | | 11/1991 | Hardenbrook et al. ... 250/458.1 |
| 5,073,488 A | | 12/1991 | Matner et al. ............ 435/31 |
| 5,087,659 A | | 2/1992 | Fujisawa |
| 5,089,659 A | | 2/1992 | Brueckner et al. ......... 560/238 |
| 5,200,147 A | * | 4/1993 | Augurt .................... 422/56 |
| 5,206,118 A | * | 4/1993 | Sidney et al. ............ 430/343 |
| 5,254,473 A | | 10/1993 | Patel ..................... 436/1 |
| 5,304,468 A | | 4/1994 | Phillips et al. ............ 435/14 |
| 5,344,017 A | | 9/1994 | Wittrock ................. 206/459 |
| 5,374,813 A | | 12/1994 | Shipp .................... 235/375 |
| 5,451,372 A | | 9/1995 | Larsson et al. ............ 422/58 |
| 5,463,213 A | | 10/1995 | Honda ................... 235/468 |
| 5,476,792 A | | 12/1995 | Ezrielev et al. |
| 5,482,684 A | | 1/1996 | Martens et al. ........... 422/119 |
| 5,576,528 A | | 11/1996 | Chew et al. .............. 235/469 |
| 5,610,811 A | | 3/1997 | Honda ................... 395/202 |
| 5,619,029 A | | 4/1997 | Roxby et al. ............. 235/472 |
| 5,623,810 A | | 4/1997 | Dey et al. ................ 53/425 |
| 5,631,171 A | * | 5/1997 | Sandstrom et al. ........ 436/518 |
| 5,635,403 A | | 6/1997 | Bailey ................... 436/66 |
| 5,636,763 A | | 6/1997 | Furness .................. 222/54 |
| 5,653,938 A | | 8/1997 | Faries, Jr. et al. ......... 422/3 |
| 5,659,345 A | | 8/1997 | Altendorf ................ 347/87 |
| 5,732,529 A | | 3/1998 | Dey et al. ................ 53/389.2 |
| 5,745,039 A | | 4/1998 | Hof et al. ................ 340/590 |
| 5,780,098 A | | 7/1998 | Battles .................. 427/2.1 |
| 5,863,790 A | | 1/1999 | Bolea ................... 435/287.4 |
| 5,882,611 A | | 3/1999 | Williams et al. .......... 422/292 |
| 5,887,716 A | | 3/1999 | Williams et al. .......... 206/459.1 |
| 5,945,341 A | * | 8/1999 | Howard, III .............. 436/46 |
| 5,990,199 A | | 11/1999 | Bealing et al. |
| 6,063,591 A | * | 5/2000 | Bolea .................... 435/31 |
| 6,180,409 B1 | * | 1/2001 | Howard, III et al. ........ 436/46 |
| 6,238,623 B1 | * | 5/2001 | Amhof et al. ............. 422/58 |
| 6,440,744 B1 | * | 8/2002 | Ignacio et al. ............ 436/1 |
| 6,454,874 B1 | * | 9/2002 | Jacobs et al. ............. 134/18 |
| 6,485,978 B1 | * | 11/2002 | Kirckof et al. ............ 436/1 |
| 6,488,890 B1 | * | 12/2002 | Kirckof .................. 422/56 |

OTHER PUBLICATIONS

U.S. Appl. No. 09/369,098, filed Aug. 05, 1999, Kippenhan et al.

U.S. Appl. No. 09/368,742, filed Aug. 05, 1999, Steven S. Kirckof.

U.S. Appl. No. 09/369, 108, filed Aug. 05, 1999, Hehenberger et al.

* cited by examiner

STERILIZATION
INDICATORS

STEAM VACUUM ASSIST

EXPOSURE CONTROL

PACKS SECURED WITH 3M COMPLY INDICATOR TAPE NO.1222

LOAD CONTROL

3M RAPID ATTEST BIOLOGICAL INDICATORS NO. 1292

EQUIPMENT CONTROL

3M COMPLY BOWIE DICK PACK NO.1233

PACK CONTROL

3M COMPLY STERIGAGE STEAM CHEMICAL INTEGRATOR NO. 1243 A OR B

Fig. 24

WARNING!

PACK NO. 9999's CHEMICAL INDICATOR

READOUT IS INCONSISTENT WITH:

PACK NO. 8888's CHEMICAL INDICATOR (SAME LOAD NO 410)

LOAD BIOLOGICAL INDICATOR NO.

410's BIOLOGICAL INDICATOR NO.

DO NOT USE CONTENTS BEFORE CONTACTING CENTRAL STERILIZATION

STEAM VACUUM ASSIST

◉ CREATE A BAR CODE CHEMICAL INDICATOR FOR PACK NO. 99991

○ SUGGEST STERILIZATION INDICATOR SELECTION

[ ENTER ]

[ QUIT ]

Fig. 27

SURGICAL ARTICLES
STERILIZATION HISTORY

ID#         NAME

4893I       METZENBAUM
                CLAMP

LAST STERILIZED JUNE 3, 1999

SUBJECTED TO [5] PREVIOUS
STERILIZATION CYCLES

LAST CYCLE READOUTS

BIOLOGICAL INDICATOR?   OK

PACK CHEMICAL INDICATOR?   OK

LOAD CHEMICAL INDICATOR?   OK

Fig. 28

CHEMICAL INDICATOR READER

FIELD

This invention relates to sterilization indicators, sterilization information and methods of monitoring articles to be sterilized. The present invention relates particularly to a sterilization indicator that can be machine read to provide a user with information relating to a sterilization process. With the present invention, information relating to the efficacy of a sterilization cycle can be machine read and/or electronically linked to integrated electronic information systems throughout the health care provider system.

BACKGROUND

Sterilization is the act of killing bacteria and other microorganisms on surgical instruments, devices and implants. Sterilizers are designed to kill all viable living organisms within a sterilization chamber. This is challenging, as objects can be contaminated with any of a number of different types of bacteria, some more dangerous and tougher to kill than others.

Sterilization indicators show whether a sterilizer achieved adequate (e.g. lethal) conditions. One kind of sterilization indicator is known as a chemical indicator. Chemical indicators respond to one or more of the critical parameters of a sterilization process. Typically, chemical indicators either change color or have a moving front with an endpoint to provide information concerning the sterilization process.

The Association for the Advancement of Medical Instrumentation {AAMI} has recommended practices and standards that cover sterilization testing, including the use of chemical indicators. Hospitals frequently look to AAMI to establish sterilization assurance procedures. See e.g. *Good Hospital Practice: Steam Sterilization and Sterility Assurance*, AAMI Recommended Practice, Section 6.4 (1988). Hospitals also look to other standards and regulatory agencies for validation, routine control and other procedures for obtaining, recording, and interpreting data to show that a sterilization process complies with a predetermined sterility assurance level. Other recommendations and guidelines are provided by the Joint Commission on Accreditation of Hospitals (JCAH), the Center for Disease Control, Association of Operating Room Nurses (AORN), American Society for Healthcare Central Services Personnel (ASHCSP), and the various state laws.

AAMI categorizes chemical indicators in five classes. See *Sterilization of health Care Products—Chemical Indicators—Part 1: General Requirements*, American National Standards Institute (ANSI)/AAMI ST 60-(1996). Class 1 relates to process indicators. Process indicators are intended for use with individual packs to demonstrate that the pack has been exposed to the sterilization process and to distinguish between processed and unprocessed packs. Class 2 describes indicators for use in a specific test procedure such as a Bowie-Dick test. Class 3 relates to single parameter indicators, and class 4 to multi-parameter indicators. Multi-parameter indicators are designed to respond to two or more critical parameters of sterilization and indicate exposure to a sterilization cycle at stated values of the chosen parameters. For example, time, temperature and saturated steam are critical conditions for a steam cycle. Class 5 chemical indicators are known as integrating indicators. These are indicators designed to react to all critical parameters over a specific range of sterilization cycles.

Integrating chemical indicators are described in U.S. Patent Reexamination Certificate No. B1-3,981,683, (Larsson et al.) and U.S. Patent Reissue No. 34,515 to Foley. Other chemical indicators are described in U.S. Pat. Nos. 3,114,349; 3,313,266; 3,341,238; 3,652,249; 4,138,216; 4,382,063; 4,576,795; 4,692,307; 4,579,715; and 5,451,372 (the entire contents of each of which are herein incorporated by reference).

Another kind of sterilization indicator is known as a biological indicator. Biological indicators use a large number (usually a million or more) of microorganisms that are highly resistant to the sterilizing agent of the sterilization cycle being monitored. See *Sterilization of Health Care Products—Biological Indicators—Part 1: General Requirements*, ANSI/AAMI ST 59 (incorporated herein by reference). Biological indicator technology is also disclosed in U.S. Pat. Nos. 3,661,717 and 5,073,088 (the entire contents of which are herein incorporated by reference).

Minnesota Mining and Manufacturing Company (3M) sells Attest™ Rapid Readout Biological Monitoring Systems. These systems include a biological indicator that is capable of exhibiting fluorescence after a failed (non-lethal) sterilization cycle, and an auto reader. To test a steam sterilizer with an Attest system, the user places the biological sterilization indicator into the steam sterilizer along with the items to be sterilized. After the sterilization cycle, the indicator is placed in an Attest auto reader (e.g. model 190). The auto reader has an incubator and a means for reading the biological indicator to determine whether the sterilization indicator exhibits fluorescence. If the steam sterilization cycle was lethal, the auto reader will not detect fluorescence within a predetermined time. If the cycle was non-lethal, the auto reader will detect fluorescence associated with the biological sterilization indicator in the predetermined time. Even with this instrumentation, a user is required to manually record the results provided by the auto reader.

Other international standards organizations and regulatory agencies describe sterilization indicators for monitoring sterilization processes in the health care context. The International Organization for Standardization (ISO) includes many standards similar to those described above. See ISO 11140-1:1995 for chemical indicators. European Standard Nos. EN 867-1 and 866-1 also include many standards similar, but not identical to those of AAMI and ISO (see e.g. The European Committee for Standardization's European Standard No. EN 867-1, *Non-biological systems for use in sterilizers*—Part 1: General requirements).

When a U.S. hospital designs its sterilization assurance practices, it often evaluates equipment control, exposure control, pack control and load control. Equipment control evaluates sterilizer performance. For example, a Bowie-Dick pack can indicate the failure of the vacuum portion of a steam sterilization cycle. Load control is often a biological indicator placed in the sterilization chamber.

Items to be sterilized are often wrapped in sterilization wrap. The wrap is typically secured with an exposure control indicator (e.g. indicator tape). The resultant assembly is referred to as a pack. Exposure control is typically a chemical indicator placed within the sterilization chamber but outside the pack that is being sterilized. Exposure control identifies processed from unprocessed packs. Pack control is usually a sterilization indicator placed within a pack that evaluates conditions inside an individual pack. After a successful sterilization cycle, the articles within the sterilization packs remain sterile until the pack is opened. As a result, packs are usually opened in a specially prepared and maintained sterile field in the operating room just prior to their use. However, commercially available sterilization indicators found within packs cannot be read prior to opening the pack because sterilization wrap is typically opaque. If the sterilization indicator inside a pack indicates a failed sterilization cycle, there are many problems in finding out about it just prior to use of the items within the pack. The problems are multiplied when the sterilization indicator identifying a failure is found within the specially prepared and maintained sterile field.

The importance of sterilization assurance in hospitals requires constant attempts to better utilize sterilization indicators. A user typically visually inspects chemical indicators to obtain information from the indicator. Some users find it difficult to subjectively determine whether a chemical indicator has changed color. This is particularly a problem for a user who suffers from color blindness. For example, some persons who suffer from color blindness have difficulty distinguishing red colors from green colors. The Propper Gas-Chex® Steri-Dot Indicators (Model No. 361001) change from a red color to green upon exposure to ethylene oxide gas. This color change may be difficult for some users to distinguish with the attendant risk of inaccurate recordation of sterilization information. Another indicator with a color change that is difficult to perceive is the Surgicot® Version 3.0 Universal Integrator. This integrator includes a steam color change bar from yellow to brown. The contrast between these particular colors is difficult for some users to perceive.

Biological indicators suffer from some of the same problems as chemical indicators. U.S. Pat. Nos. 5,030,832; 5,063,297; 5,334,841 and 5,863,790 (the entire contents of each of which are herein incorporated by reference) describe electronic reading apparatus for objectively reading fluorescence of biological indicators.

Accuracy of information relating to the state of objects in the sterilization process at a healthcare facility (e.g. a hospital) is very important. Access to this information is also important. There are many ways that human error can adversely affect a hospital's sterilization assurance procedures. Operators can err in capturing data (e.g. transpose numbers, improperly key-in information to a computer), perceiving information (e.g. the color blindness issue discussed above) and recording data, to name just a few. Because sterilization indicators are small, they can simply become lost, especially if their use entails transportation between different hospital functions, locations or departments.

Despite the importance of this information and the problems noted above, the recordation or management of information relating to sterilization in U.S. hospitals today usually includes several subjective, manual steps. For example, forms are manually filled out with a pen or pencil, or a sterilization indicator is subjectively inspected for color change, or the information is manually typed into a database. When a hospital utilizes several different types of sterilizers (e.g. steam sterilizers, flash steam sterilizers, ethylene oxide sterilizers or vapor phase hydrogen peroxide sterilizers), it makes the recording problem even more complex. To address the problems mentioned above, hospitals invest in significant and costly training of personnel responsible for sterilization monitoring.

There are many sterilization article tracking systems reported in the literature. U.S. Pat. No. 3,568,627 discloses a combined record card and sterilization indicator. German Utility Model (Gebrauchsmuster) No. G 90 04 818.0 (assigned to Vereinigte Papierwarenfabriken GmbH) discloses a label for sterile packaging. However, these require manual steps associated with the sterilization information tracking.

Bar codes are used extensively in the health care industry. See Adams et al., *Bar Coding: An Effective Productivity Concept*, JONA, Vol. 21, No. 10 (October 1991); and Weilert et al., *Putting Bar Codes to Work for Improved Patient Care*, Clinics in Laboratory Medicine, Vol. 11, No. 1 (March 1991). German Patent Application No. DE 3917876 discloses a bar code on a surgical instrument. U.S. Pat. No. 5,635,403 describes a tracking and identification card for an air filter specimen that includes a bar code. U.S. Pat. No. 5,653,938 discloses bar codes used in a method for ensuring sterility of surgical drapes. Such bar codes comprise a permanent, colorfast black ink, as opposed to a sterilizing agent sensitive ink (e.g. one that changes colors during a sterilization cycle).

European Patent Application No. 630 820 discloses a process and system for monitoring material flow during the preparation of sterile goods. This inventory system utilizes bar codes to help track objects to be sterilized. U.S. Pat. Nos. 5,374,813 and 5,610,811 describe surgical instrument tracking systems that make use of bar codes. None of these bar codes include a sterilizing agent sensitive ink.

Some hospitals utilize computerized inventory management systems that require a user to manually key in data relating to the status of a sterilization indicator. For example, in the same sterilization load, a biological indicator, chemical indicators and a test pack may be used. The prior art inventory management systems require the user to manually input a great deal of data relating to these different types of sterilization indicators with the attendant risk that the user will improperly record the information or fail to record it at all. For example, a user may manually type in information relating to whether the indicator shows "pass" or "fail" of the sterilization cycle. The difficulty associated with accurately recording sterilization information is exacerbated by the fact that chemical indicator information is typically recorded just after a sterilization cycle while biological indicator information is recorded many hours or days after the sterilization cycle.

The art is also replete with electro-optical devices for reading items. Examples of such devices are described in U.S. Pat. Nos. 5,351,078; 5,576,528 and 5,619,029. Canadian patent No. 1,204,300 (Prusik et al.) describes an electro-optical device for reading a bar code. The bar code is said to be useful for, inter alia, assessing time-temperature exposures of environmental indicating devices that are attached to products which experience progressive quality changes as they are subjected to certain temperatures over certain periods of time. Prusik et al. does not disclose a chemical indicator for use in monitoring a sterilization procedure at a health care facility.

Sterilization indicators and labels for articles to be sterilized are typically manufactured at a location remote from their actual use. Thus, the type and design of sterilization indicators are dictated by the manufacturer, not by users. Moreover, users do not have the ability to generate their own indicators. As a result, hospitals today are required to order and ship very specific types of indicators that are not hospital/site specific. There is little chance for customization of the indicator at the hospital. As a result, some hospitals even customize information on existing labels with manual printable pens to capture information such as pack content, intended location and targeted use.

SUMMARY OF THE INVENTION

The present invention comprises a sterilization indicator and monitoring method that affords the user the ability to: a)

acquire, store and use sterilization monitoring information quickly and cost effectively without the delay, cost and inaccuracy associated with prior art sterilization indicators, b) reduce sterile products inventory hold time, increase the accuracy of information storage and provide higher levels of accuracy in data management, c) possess a unified, integrated sterility assurance and inventory management system, d) minimize the potential for human error in a system for monitoring the sterilization of articles, and e) customize sterilization assurance information for site specific needs.

In one aspect, the present invention comprises an apparatus for reading a chemical indicator for monitoring a sterilization process. The chemical indicator comprising a substantially flat surface and a sterilizing agent sensitive ink associated with the surface. The ink provides a first indicating state prior to being exposed to the sterilization process, and a second indicating state after being exposed to at least a portion of the sterilization process.

The apparatus includes an illumination source for directing energy toward the surface; a detector for collecting energy reflected from the surface and for providing a signal based on the energy from the surface; positioning means for positioning the surface of the chemical indicator relative to the illumination source and the detector; a controller for controlling the detector and illumination source; and processing means for processing the signal from the detector, for distinguishing the first and second states, and for determining whether the chemical indicator is in said first or said second state.

BRIEF DESCRIPTION OF THE DRAWINGS

The present invention will be further described with reference to the accompanying drawing wherein like reference numeral refer to like parts in the several views, and wherein:

FIG. 24 is a view of a computer screen of the sterilization monitoring tracking system of FIG. 21 after "Sterilization Indicators" and a particular type of sterilization procedure have been selected;

FIG. 26 is a view of a computer screen of a sterilization monitoring tracking system showing an example of a warning and further instructions that may be provided to a user;

FIG. 27 is a view of a computer screen of a sterilization monitoring tracking system that allows a user to create his or her own chemical indicator or to obtain information relating to sterilization indicator selection;

FIG. 28 is a view of a computer screen of a sterilization monitoring tracking system showing a particular item's sterilization history;

DETAILED DESCRIPTION

Figure 1:
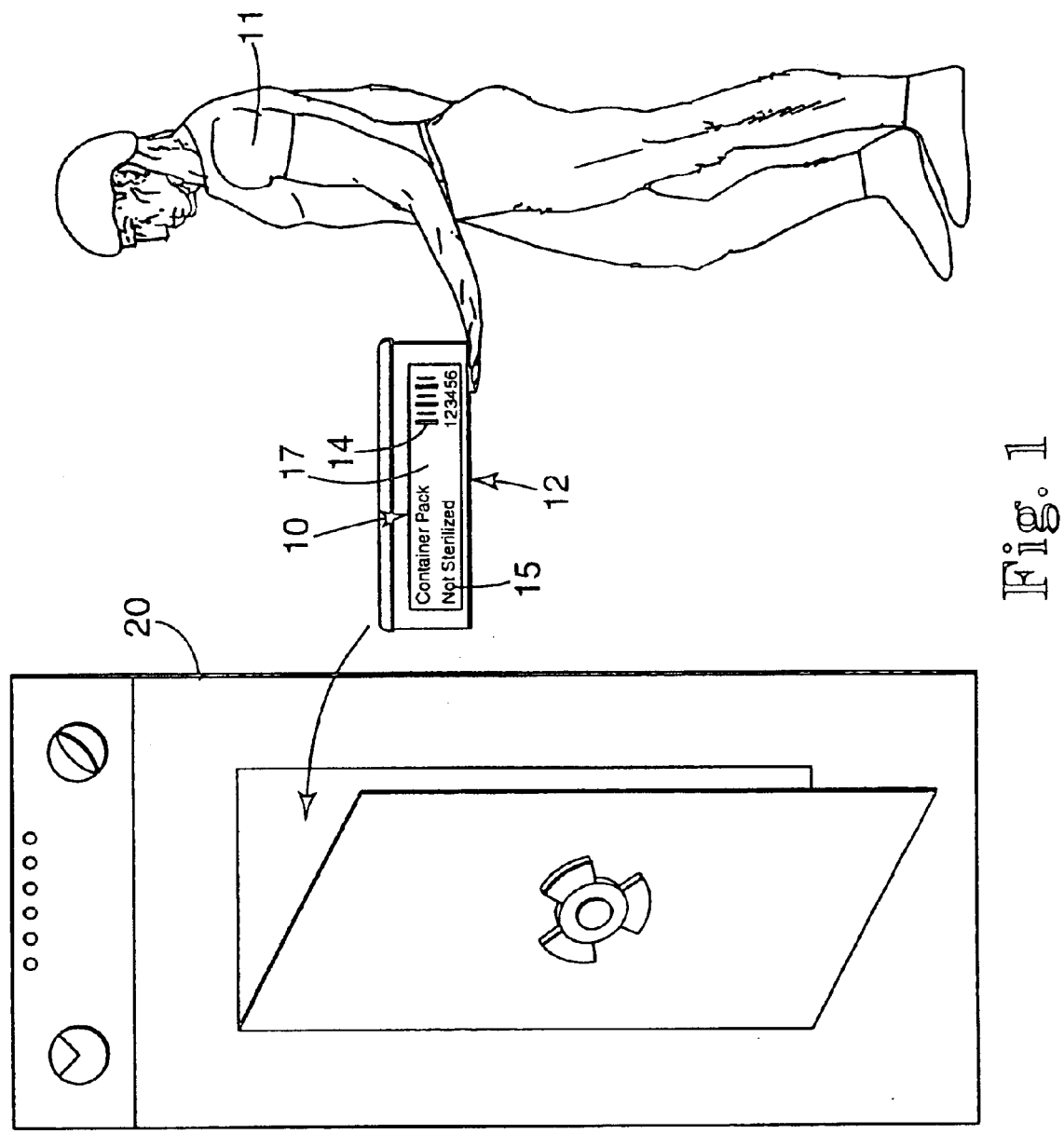
FIG. 1 is a schematic view of the present invention showing a container pack with a sterilization indicator code being placed into a sterilizer.
Figure 2:
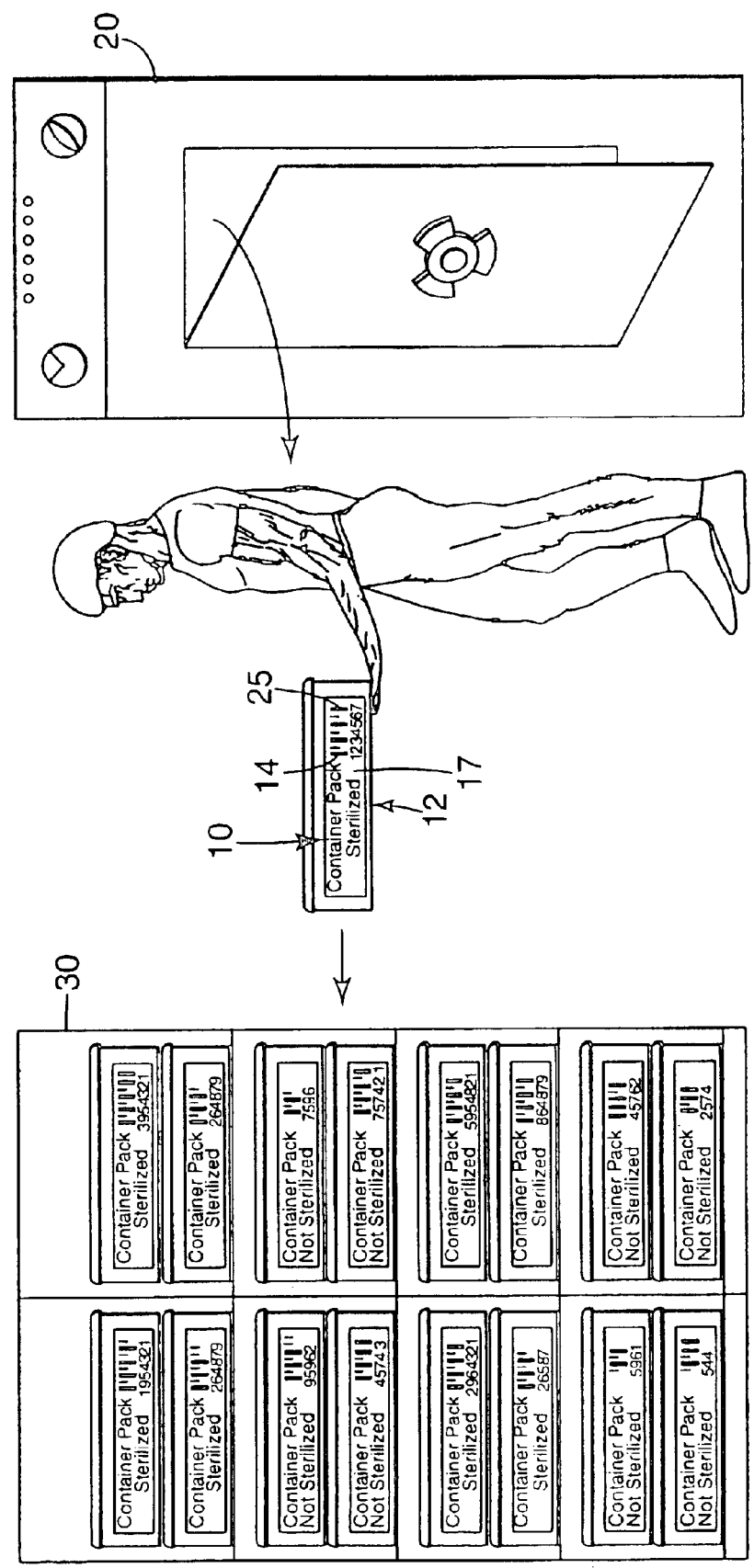
FIG. 2 is a schematic view showing the container pack of FIG. 1 being removed from the sterilizer and placed into storage.

Referring now to FIGS. 1 and 2, there is shown a preferred embodiment of sterilization indicator or monitor 10 according to the present invention. The sterilization indicator 10 monitors the effectiveness of a sterilization process provided by sterilizer 20.

The sterilizer 20 can conduct any one of a wide variety of sterilization processes including those sterilization procedures that utilize different sterilizing agents such as hydrogen peroxide, peracetic acid, glutaraldehyde, ozone, steam, dry heat, ethylene oxide, formaldehyde, and gamma irradiation as a sterilant or as an element in a step in the procedure, and those sterilization procedures which utilize combinations of such sterilizing agents. The present invention may be practiced with procedures that utilize matter in a variety of states such as liquids, gases, fluids, plasmas and sterilization procedures that utilize combinations of those states. For example, the sterilizer 20 may utilize hydrogen peroxide. As used herein, vapor phase, liquid phase and plasma hydrogen peroxide sterilization procedures are all within the broad definition of hydrogen peroxide sterilization procedures. Sterilization procedures that utilize hydrogen peroxide as merely a component during a substantial portion of the procedure are also included within the meaning of the phrase "hydrogen peroxide sterilization procedure". U.S. Pat. Nos. 4,169,123; 4,169,124; 4,642,165; 4,643,876, 4,744,951; 4,756,882; 4,943,414; and 5,667,753 all describe hydrogen peroxide sterilization procedures and the entire contents of each of them are herein incorporated by reference.

The sterilization indicator 10 is preferably capable of being read by a code reader (e.g. a bar code reader). The sterilization indicator 10 comprises a substrate or backing having a surface 17, and sterilizing agent sensitive means 25 (see FIG. 2) for responding to a sterilization process. The sterilizing agent sensitive means could be white ink printed on the surface 17 of a white substrate at a predetermined position and pattern. The ink is preferably sized, shaped and oriented in a predetermined manner, such as a portion of a bar code. The ink could be designed to change its initial white color to black after a sterilization procedure.

As used herein, "sterilizing agent sensitive means for responding to a sterilization process" means a composition that is capable of having a first indicating state prior to being exposed to a predetermined sterilization procedure and a second indicating state after exposure to at least a portion of the sterilization procedure (preferably the entire sterilization procedure). Preferably, the first indicating state of the composition is a first color and the second indicating state of the composition is a second color that is different than the first color. The first state could also be a substantially clear or transparent or translucent state, and the second state could be a substantially opaque or colored state. The converse of these states could also be employed.

Figure 32:
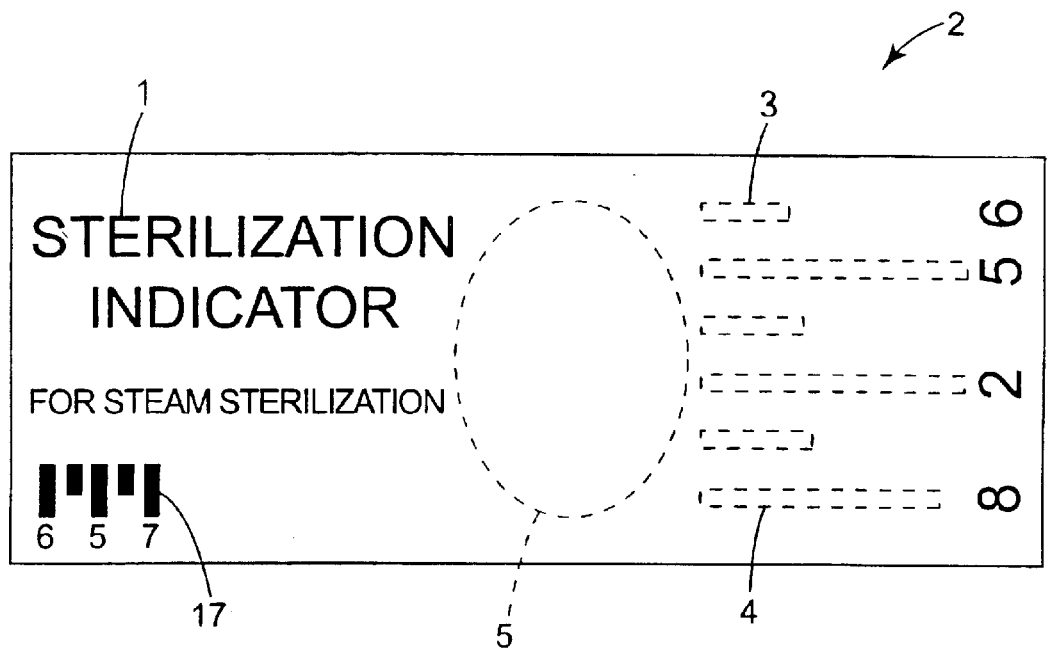
FIG. 32 is a top view of an embodiment of a sterilization indicator according to the present invention prior to being subjected to a sterilization cycle.
Figure 33:
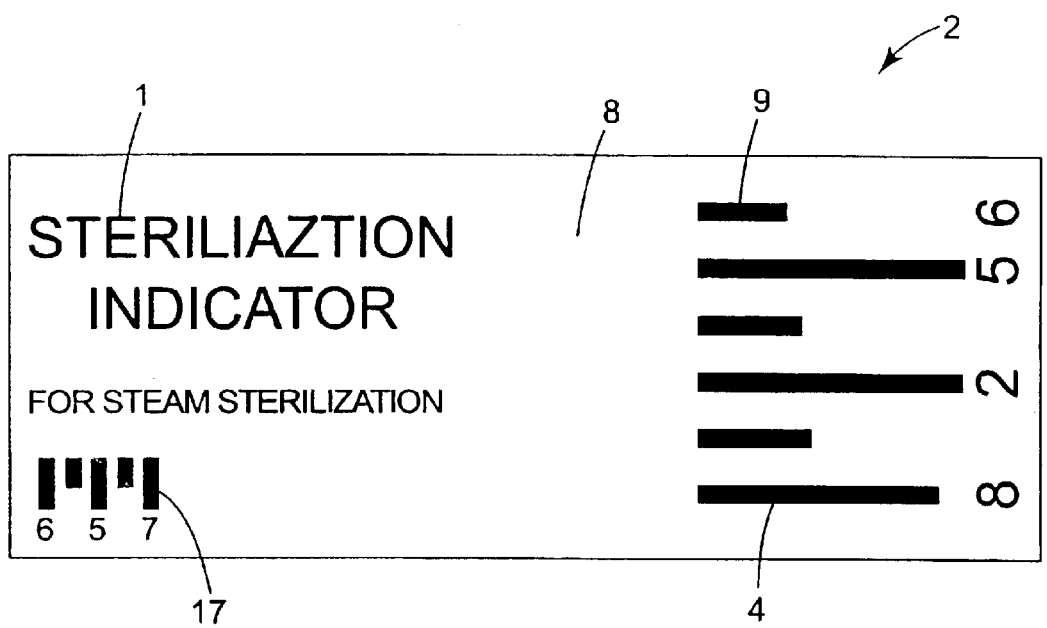
FIG. 33 is a top view of the sterilization indicator of FIG. 32 after the indicator is subjected to a sterilization cycle.

FIGS. 32 and 33 show an alternative embodiment of the present invention. FIG. 32 is a top view of a sterilization indicator 2 prior to being subjected to a sterilization cycle in sterilizer 20 (FIG. 1). In the sterilization indicator 2, the sterilizing agent sensitive means for responding to a sterilization process comprises a tablet 5 that wicks along a backing 3 using the components of the indicators described in U.S. Patent Reexamination Certificate No. B1-3,981,683, (Larsson et al.) and U.S. Patent Reissue No. 34,515 to Foley (the entire contents of the file histories of the patents, the Reexamination and Reissue are herein incorporated by reference).

The top of the indicator 2 includes a surface 8 with a cutout or window 4 that is in the size and shape of a bar code. The frame of the window 4 is the appropriate size or shape (e.g. width) so that the sterilization indicator 2 may be read by a code reader after sterilization. However, because the backing 3 is substantially the same color as the surface 8 (e.g. white), the bar code is initially substantially indescernible prior to being subjected to a sterilization process.

FIG. 33 is a top view of the sterilization indicator 2 after it is subjected to a sterilization cycle. The tablet 5 has melted and wicked along backing 3. When melted, the tablet 5 is a different color than the backing 3. As a result, the bar code 9 becomes readable by a reader due to the color of the melted tablet 5.

Optionally, the sterilization indicator 2 could include a bar code 17 printed from a colorfast, permanent ink that can be used for inventory purposes. The indicator 2 may also include other indicia 1.

There are a wide variety of suitable indicating compositions for use in conjunction with the variety of sterilization procedures mentioned above. Suitable compositions (and other components) for the sterilization indicator 10 are described in U.S. Pat. Nos. 2,118,144; 2,937,279; 3,098,751; 3,258,312; 3,311,084; 3,360,337; 3,360,338; 3,360,339; 3,386,807; 3,523,011; 3,627,469; 3,667,916; 3,684,737; 3,852,034; 3,862,824; 4,155,895; 4,138,216; 4,015,937; 4,094,642; 4,165,399; 4,166,044; 4,179,397; 4,168,779; 4,188,437; 4,240,926, 4,382,063; 5,057,433; 5,064,576; 5,087,659; 5,451,372; and 5,316,575 (the entire contents of each of which are herein incorporated by reference). UK Patent Nos. 1458533 and 1370470 and PCT publication no. 98/13431 also disclose suitable compositions and backings for the present invention (the entire contents of each of which are herein incorporated by reference). The literature also describes suitable compositions. See Royce and Bower, "An Indicator Control Device for Ethylene Oxide Sterilization." J. Pharm. and Pharm. 11, Suppl. 294T–298T, and Brewer et al, Journal of Pharmaceutical Sciences, pages 57–59, January 1966.

As an example for steam sterilization, there are a number of compounds having sulfur-containing radicals that will decompose (e.g. to metal sulfide) under steam sterilization conditions with a pronounced color change. Metal sulfides tend to be strongly colored and are often the most stable form of metal sulfur-containing compounds. Furthermore, they are often insoluble in water and may be held in a binder to prevent staining. The preferred sulfur-containing radical is thiosulfate although other groups may be employed, e.g., polythionates, etc. Compounds for use as the primary color change component include:

lead thiosulfate which is white in color and decomposes to yield black lead sulfide under steam sterilization conditions, copper thiosulfate which is yellow in color and decomposes to yield black copper sulfide under steam sterilization conditions, ferrous thiosulfate which is light green in color and decomposes to yield a black sulfide under steam sterilization conditions, nickel thiosulfate which is light green in color and decomposes to black/green nickel sulfide under steam sterilization conditions, cobalt thiosulfate which is light red/purple in color and decomposes to deep purple/black cobalt sulfide under steam sterilization conditions, bismuth thiosulfate which is orange/brown in color and decomposes to black bismuth sulfide under steam sterilization conditions, chromium thiosulfate which is gray/blue in color and decomposes to dark green chromium sulfide under steam sterilization conditions, and silver thiosulfate which is brown in color and decomposes to black silver sulfide under steam sterilization conditions.

Precursors of such sulfur-containing compounds may be used that will yield the sulfur-containing compounds under aqueous conditions. For example, lead carbonate and sodium thiosulfate may be employed as the color change component in the ink. These compounds undergo a double decomposition reaction to yield lead thiosulfate under aqueous conditions. During the steam sterilization cycle, lead thiosulfate is initially formed which then decomposes to lead sulfide providing the desired color change.

In the case of an ethylene oxide sterilization process, ethylene oxide is sometimes diluted with a gas inert to the ethylene oxide, such as Freon®, a fluoro-chloro substituted ethane, or $CO_2$. The Freon® selected should be a gas at the sterilization temperature. The concentration of ethylene oxide could be about 450 mg/liter to about 1,500 mg/liter, while processing temperatures can range from about 70 to about 140° F. Preferably, where the diluent is Freon®, the ethylene oxide concentration is about 12 wt. % in the sterilant gas. Where the diluent is $CO_2$, the concentration of ethylene oxide is about 10 wt. %. For such processes, the parameters which affect ethylene oxide sterilization processes are exposure time, ethylene oxide concentration, temperature and humidity. For diluted ethylene oxide, relative humidities below 30% RH limit the effectiveness of the ethylene oxide sterilization process. High humidities, e.g., above 90% RH, also results in inadequate processing.

Sterilizing agent sensitive means 25 (FIG. 2) comprising 4(4-nitrobenzyl)pyridine may be used in ethylene oxide sterilization process monitoring. See, for example, Journal of Pharmaceutical Sciences, Brewer et al., pages 57–59, January 1966. Other compounds, including pyridines and quinolines, have also been utilized.

The sterilization indicator 10 may also be one designed for use in a hydrogen peroxide sterilization procedure (e.g. the procedure provided by the Sterrad® Hydrogen Peroxide Plasma Sterilizers available from Advanced Sterilization Products of Irvine, Calif. U.S.A. Examples of indicating compositions for use in hydrogen peroxide sterilization may be found in European Patent Application Publication No. 914 833, and PCT International Publication Nos. 98/52621; 96/33242 and 98/46994 (the entire contents of each of which are herein incorporated by reference).

Alternatively, the sterilization indicator 10 may be used in a sterilization process that includes the use of a peracid liquid (e.g. the STERIS SYSTEM 1™ and Steris 20™ Sterilant Concentrate available from Steris of Mentor, Ohio U.S.A.). Suitable indicating compositions are described in PCT International Publication No. PCT/WO/98/58683 (the entire contents of which are herein incorporated by reference).

In the case of a liquid peracetic acid sterilizer 20, means 25 (FIG. 2) preferably includes a halide salt that, when subjected to an oxygen source, is oxidized to release a free halide. The free halide halogenates a dye causing it to change from a first color to a second color. The preferred halide is a salt of an alkali or alkaline earth metal, e.g., potassium bromide. A suitable dye is phenol red, preferably the sodium salt thereof.

The combination of dye and the alkali metal or alkaline earth halide may be applied to a substrate in a suitable medium (e.g. by flexographic printing). The substrate may optionally be any substrate through which the sterilant can diffuse. Exposure of the substrate to the sterilization process should not adversely affect the sterilization process by, for example, excessively absorbing sterilant. Polymeric materials or coatings are useful to prevent excessive absorption of sterilant. For convenience of use, the substrate could be an elongated strip of material with the indicator composition printed in a bar code at one end. This allows the remainder of the strip to act as a handle by which the indicator can be held.

Indicating compositions for a peracetic acid sterilizer 20 may comprise a colorant susceptible to halogenation. Such an indicating ink may comprise fluorescein and/or phenol red. When phenol red is used as the dye and a bromine salt is used, the pH of the paper is preferably at least 5.0, preferably at least 5.2. This is because the bromophenol blue formed has a pK of about 4. Below 4, the bromophenol blue is yellow, and above 4 the dye is blue. The phenol red, on the other hand, has a pK of about 7.9. The pH of the paper, which is to have a yellow starting color where the dye is phenol red, can be about 5.0 to about 7.5. Where this pH range is used, the pH is fortuitously above the pK of the bromophenol blue, and, hence, the bromophenol blue formed where a bromide is the halide will have a blue appearance. The contrast between the initial yellow color of the phenol red and the final blue color of the bromophenol blue is sharp.

Illustrative non-limiting examples of alkaline earth halide salts useful for a sterilization indicator 10 for peracetic acid procedures include magnesium bromide, magnesium chloride, and potassium bromide. Each salt should be associated with a dye that can be halogenated by free halogen liberated by the reaction of halide with the peracetic acid. The resulting halogenated dye should have a color that is distinguishable from the dye selected as the starting material to be halogenated. Dyes having those required characteristics can be readily selected based on their chemical properties. There are numerous reference books listing dyes and their chemistry, illustrative of which is *H.J Conn's Biological Stains*, 8th Edition, Lillie, R. D., The Williams & Wilkins Co., Baltimore, Md. (1969) (incorporated herein by reference).

Illustrative non-limiting examples of dyes suitable for use in a sterilization indicator 10 with a sterilization agent sensitive means 25 are phenol red, fluorescein, ethyl red, thymol blue, Acid Fuchsin, m-cresol purple, bromophenol blue, bromocresol green, and cresol red. Each dye can be used in combination with magnesium bromide applied to a backing and exposed to hydrogen peroxide vapor, which results in the color changes indicated in following chart:

| Dye | Initial Color | Color Change |
| --- | --- | --- |
| Ethyl Red | Light Pink | Light Yellow |
| Thymol Blue | Yellow-Orange | Light Yellow |
| Bromothymol Blue | Yellow | Yellow |

-continued

| Dye | Initial Color | Color Change |
|---|---|---|
| m-Cresol Purple | Faded Yellow | Sky Blue |
| Bromophenol Blue | Yellow | Light Blue |
| Bromocresol Purple | Yellow | Faded Yellow |
| Bromocresol Green | Yellow | Yellow-Green |
| Cresol Red | Light Yellow | Lighter Yellow |

The sterilization indicator 10 may include any backing or substrate that is compatible with the particular sterilization environment. Additionally, the substrate should be capable of withstanding the predetermined sterilization environment. For example, in the case of steam sterilization conditions, the backing is preferably capable of withstanding a temperature of 110° C. to 142° C., in the presence of steam for a period of up to 30 minutes. Suitable substrates include paper which may be absorbent or saturated with a rubber/resin solution or a natural or synthetic latex, coated paper, card, plastics material, metallised material, metal foil, and non-woven or woven textile materials. In the case of hydrogen peroxide sterilization procedures, the backing should not absorb excessive amounts of hydrogen peroxide. Excessive absorption of hydrogen peroxide can result in cycle shut down or an inaccurate sterilization indication by the sterilization indicator 10.

Other suitable backings can be made from any non-water-dispersible film, paper, or other material physically capable of withstanding the conditions of a given sterilization cycle. Non-limiting examples of other suitable backings include isotactic polypropylene backings, such as disclosed in U.S. Pat. No. 4,898,762, as well as latex-saturated paper backings, foil backings, woven and non-woven backings, polyolefin-based film backings, such as polyethylene backings, and also polyester film backings. For example, a backing could comprise a 29 pound basis weight Kraft paper (M–2383 Smooth Crepe Semi-Bleached Kraft Saturating Paper; Mosinee Paper Corporation, Mosinee, Wis.). Other backing materials are disclosed in U.S. Pat. Nos. 4,301,195; 4,537,405; 4,956,230 and 5,679,190 (the entire contents of which are herein incorporated by reference).

Some sterilization indicators 10 may optionally include top coatings. The top coating could be substantially transparent and could substantially prevent/minimize diffusion of reactive chemicals (chemicals which react mainly with the means 25 or affect the rate/nature of reaction) in the atmosphere. The top coating is also helpful in reducing any harmful effect of other ambient conditions, such as humidity, ultraviolet light, and pollutants. The top coat can be coated from solution/emulsion or laminated. A binder material can also be a top coat.

When the present invention refers to a sterilizing agent sensitive means being associated with a substrate, it includes both situations where the sterilization indicator includes one or more coatings on top of the indicator composition as well as situations where the sterilization indicator includes no coatings on top of the indicator compositions. Representative examples of the optional top coating are synthetic polymers such as polyethylene, polypropylene, polyesters, polydienes, polyvinylacetate, polyurethane, polyamides, polyethyleneglycol, polystyrenes, polyacrylates, polymethacrylates, polyacrylamides, polyvinylfluorides, fluorinated polymers and copolymers, polyvinyl esters, teflons, polytetrafluoroethylenes, polyoxides, polycarbonates, polyvinylchloride, polysiloxanes, and natural polymers such as derivatives of cellulose and starch and gelatin and mixtures thereof. The selection of the top coating material is, of course, dependent upon the sterilization environment because the top coating should preferably be compatible with and capable of withstanding the sterilization environment. Additionally, the top coating should not adversely affect the second indicating state (e.g. color) of the means 25 after sterilization nor should it interfere with detection by the reader.

The top coating material may be coated on the backing surface including the ink mixture by any conventional coating technology. Common technologies include air knife, brush, colander, cast coating, curtain, dip, extrusion, piezoelectric, continuous inkjet, blade, knife coating, gravure, kiss roll, off-set, reverse roll, rod, spray and squeeze roll, to name a few. See, Coeling, K. J. and Bublick, T. J., Encycl, Polym. Sci. Eng., Vol. 3, 552–615 (1986). One preferred method is screen printing.

The identifying indicia or code may be formed from an ink mixture including an ink composition, as described above, and at least one optional additive, such as a binder, a solvent or both. Upon application of the ink to the backing, the solvent evaporates leaving behind the active ingredients bound together and to the substrate by the binder.

The optional binder should be compatible with the ink. One example of a preferred binder includes 24% nitrocellulose ethyl alcohol (Hercules Inc., Wilmington, Del.); 3% phenol-formaldehyde resin (BECKCITE™ 24-102, BTL Specialty Resins, Toledo, Ohio); 9% tricresyl phosphate; 14% butyl alcohol; 27% xylene, and 23% butyl acetate.

Optionally, the sterilization indicator 10 may comprise a label with a suitable adhesive. The sterilization indicator 10 shown in FIGS. 1 and 2 is shown as a part of a label applied to a sterilization pack 12. Labels are particularly useful in distinguishing packs 12 stored in a storage means 30, such as a shelf or cart. Suitable-adhesives for labels for use in sterilization processes are described in Amhof et al., U.S. patent application Ser. No. 09/019,445 filed Feb. 5, 1998 (the entire contents of which are herein incorporated by reference). Alternatively, the sterilization indicator 10 with a bar code can comprise a label placed on a bioligical indicator (e.g. the vial of a biological indicator). While the sterilization indicator 10 is suitable for use as a label or sterilization indicator tape, it is appreciated that the sterilization indicator 10 can also be an indicator without an adhesive as well.

The sterilizing agent sensitive means 25 is preferably arranged in at least a portion of a code. In FIG. 2, the means 25 forms a portion of a bar code 14. In one embodiment of the present invention, the bar code 14 may be partially formed of a permanent or colorfast ink (i.e. an ink that is not sensitive to the sterilizing agent of a sterilization process). In this embodiment of the present invention, a portion of the bar code remains substantially the same color both before and after being exposed to a sterilization process.

In an alternative embodiment of the present invention, the entire bar code may be printed from sterilizing agent sensitive ink that changes color upon exposure to a sterilization process. In this alternative embodiment, the scanning device used to read the sterilization indicator is preferably able to distinguish the first and second colors of the bar code. Depending on the use of the bar code, it may be useful (e.g. cost effective or otherwise convenient) to utilize a reader that can only read one of the two colors.

FIG. 1 shows the bar code 14 prior to being exposed to the sterilization process within the sterilizer 20. In this embodiment, the portion of the bar code 14 that is formed of the colorfast or permanent ink provides a first indication (e.g. "123456") to a bar code reader prior to the sterilization indicator 10 being exposed to the sterilization process (FIG.

1). In the embodiment of the present invention shown in FIG. 1, the means 25 is not initially readable by the scanning means. The means 25 is not readable prior to being subjected to a sterilization cycle. For example, the means 25 may comprise white sterilization indicator ink printed on white paper.

The bar code 14 provides a second indication (e.g. "1234567") to the bar code reader after the sterilization indicator 10 is exposed to a sterilization process (FIG. 2). After the sterilization process, the bar code 14 includes a portion formed of an ink that is sensitive to the sterilization process and a portion formed from an ink that is not sensitive to the sterilization process. As can be seen by comparing FIGS. 1 and 2, after the sterilization process, the white sterilization indicator ink has changed to black and added a bar on the bar code. The means 25 is now readable (after the sterilization cycle) and the bar code 14 now reads something different than it read prior to the sterilization cycle.

While the first indication (FIG. 1) provided by the sterilization indicator 10 is different than the second indication (FIG. 2), the present invention includes embodiments where the first or second state is not readable by a scanning means or bar code reader. For example, the entire bar code could optionally be comprised of a white to black steam sensitive indicator ink printed on a white background. Thus, it is appreciated that all or just a portion of the code may be formed from the sterilization agent sensitive means 25.

The sterilization indicator 10 may optionally include other forms of sterilizing agent sensitive inks. FIG. 1 illustrates an optional symbol 15 that substantially disappears or becomes substantially less prominent after a sterilization cycle. For example, the symbol 15 can be the word "NOT" printed in steam sensitive indicator ink that is initially red on a white backing. Upon exposure to a steam sterilization cycle, the ink of this embodiment of the present invention changes to a color close to the color of the backing (see FIG. 2) or clear.

As used herein, the term "code" means a predetermined image or symbol that is sized and shaped to be read by a predetermined code reader (e.g. a bar code reader), as opposed, for example, to the bar of indicating ink found on some prior art chemical indicators. The predetermined code reader is capable of reading and decoding the symbol of the code. While applicants have discovered that prior art chemical indicators may be read by specialized color reading devices (discussed in greater detail below), the prior art sterilization indicators do not include sterilization sensitive inks printed in a predetermined image or symbol that are sized and shaped to be read by a predetermined code reader.

Examples of suitable codes for use in the sterilization indicator 10 include one and two dimensional codes, bar codes, linear codes, matrix codes, discrete codes, fixed and variable length codes. An example of a suitable variable length code is Code 39. A suitable fixed length code is the Universal Product Code (UPC).

The phrase "bar code" means a symbol that is a pattern of indicia (preferably alternating parallel bars and spaces of various widths) that represents data elements or characters. For example, the bars could represent strings of binary ones (1's) and the spaces represent strings of binary zeros (0's).

The code can be printed in a variety of fashions including the use of dot-matrix printers, thermal printers, thermal transfer printers, ink jet printers and laser printers. Ink formulations may be printed by a range of printing techniques, e.g., flexographic, rotogravure, ink-jet and screen printing, etc.

A sterilization indicator 10 that includes a code may be constructed to be any of the five classes of chemical indicators found in *Sterilization of Health Care Products—Chemical Indicators—Part 1: General Requirements*, ANSI/AAMI ST 60-1996) (incorporated herein by reference in its entirety). For example, the sterilization indicator 10 may comprise a process indicator for steam sterilization and the components of the sterilization indicator 10 may be selected so that the sterilization indicator 10 satisfies the 121 degree Celsius test defined in Section 6.1 of the Sterilization of Health Care Products—Chemical Indicators—Part 1: General Requirements, ANSI/AAMI ST 60 (1996) (referencing the test methods described in ANSI/AAMI ST 45-1992, Bier/Steam vessels, which test methods are herein incorporated by reference) in that:

a) after exposure to a previously stabilized condition of dry heat at 140 degrees Celsius (plus or minus two degrees Celsius) for 30 minutes (plus or minus one minute), the sterilization indicator 10 shows either no change or a change that is markedly different from the change occurring after exposure to the steam sterilization process; and b) the second indication (e.g. the second color) shall not occur until the sterilization indicator has been exposed to saturated steam for not less than 2 minutes at 121 degrees Celsius (+31–0 degrees Celsius); and c) the second indication shall occur after the sterilization indicator is subjected to saturated steam for not more than 10 minutes at 121 degrees Celsius (+3/−0 degrees Celsius).

The components of the sterilization indicator 10 may also be selected so that the sterilization indicator 10 satisfies the 134 degree Celsius test defined in Section 6.1 of the *Sterilization of Health Care Products—Chemical Indicators — Part 1: General Requirements*, ANSI/AAMI ST 60(1996) (again referencing the test methods described in ANSI/AAMI ST 45-1992, Bier/Steam vessels) in that:

a) after exposure to a previously stabilized condition of dry heat at 140 degrees Celsius (plus or minus two degrees Celsius) for 30 minutes (plus or minus one minute), the sterilization indicator shows either no change or a change that is markedly different from the change occurring after exposure to the steam sterilization process; and b) the second indication shall not occur until the sterilization indicator has been exposed to saturated steam for not less than 20 seconds at 134 degrees Celsius (+3/−0 degrees Celsius); and c) the second indication shall occur after the sterilization indicator is subjected to saturated steam for not more than 2 minutes at 134 degrees Celsius (+3/−0 degrees Celsius).

Optionally, for purposes of steam sterilization, the components of the sterilization indicator 10 may be selected so that it satisfies both the 121 degree Celsius test and the 134 degree Celsius test defined in Section 6.1 of the *Sterilization of Health Care Products—Chemical Indicators—Part 1: General Requirements*, ANSI/AAMI ST 60—(1996). In the case of a sterilization indicator 10 for an ethylene oxide sterilization process, the ANSI/AAMI guidelines include tests for ethylene oxide sterilization processes. *Sterilization of Health Care Products—Chemical Indicators—Part I: General Requirements*, ANSI/AAMI ST 60—1996) references test methods described in ANSI/AAMI ST 44-1992 BIER/EO gas vessels, which test methods are herein incorporated by reference. The sterilization indicator 10 could be constructed to meet the guidelines for ethylene oxide sterilization processes as well.

The sterilization indicator 10 may optionally comprise an integrating indicator. That is, the chemical indicator 10 is constructed so that it reacts to all critical parameters over a specific range of a predetermined sterilization process. For a steam sterilization process, the critical parameters are time, temperature and saturated steam.

In another aspect of this invention, it has been determined that specialized scanning means are capable of reading sterilization indicators that do not have sterilizing agent sensitive means arranged in a code. As used in this specification, the phrase "scanning means" means an automatic device or machine capable of detecting first and second indicating states of a sterilization indicator. For example, the scanning means may be capable of reading the first and second states of the sterilizing agent sensitive means of a chemical indicator, or first and second readings from a biological indicator.

A "code reader" is an automatic device or machine capable of reading and decoding the symbols of a predetermined code. Thus, a code reader is a specialized form of a scanning means.

With some specialized scanning means of the present invention, the sterilizing agent sensitive means need not be in code form. Thus, "scanning means" according to the present invention includes devices that are capable of reading a sterilization sensitive ink composition in code form and also devices that are capable of reading a sterilization sensitive ink composition in non-code form (e.g. with the ink printed in a rectangle as used with some prior art sterilization indicators). Preferably, the scanning means is an electro-optical device.

Figure 17:
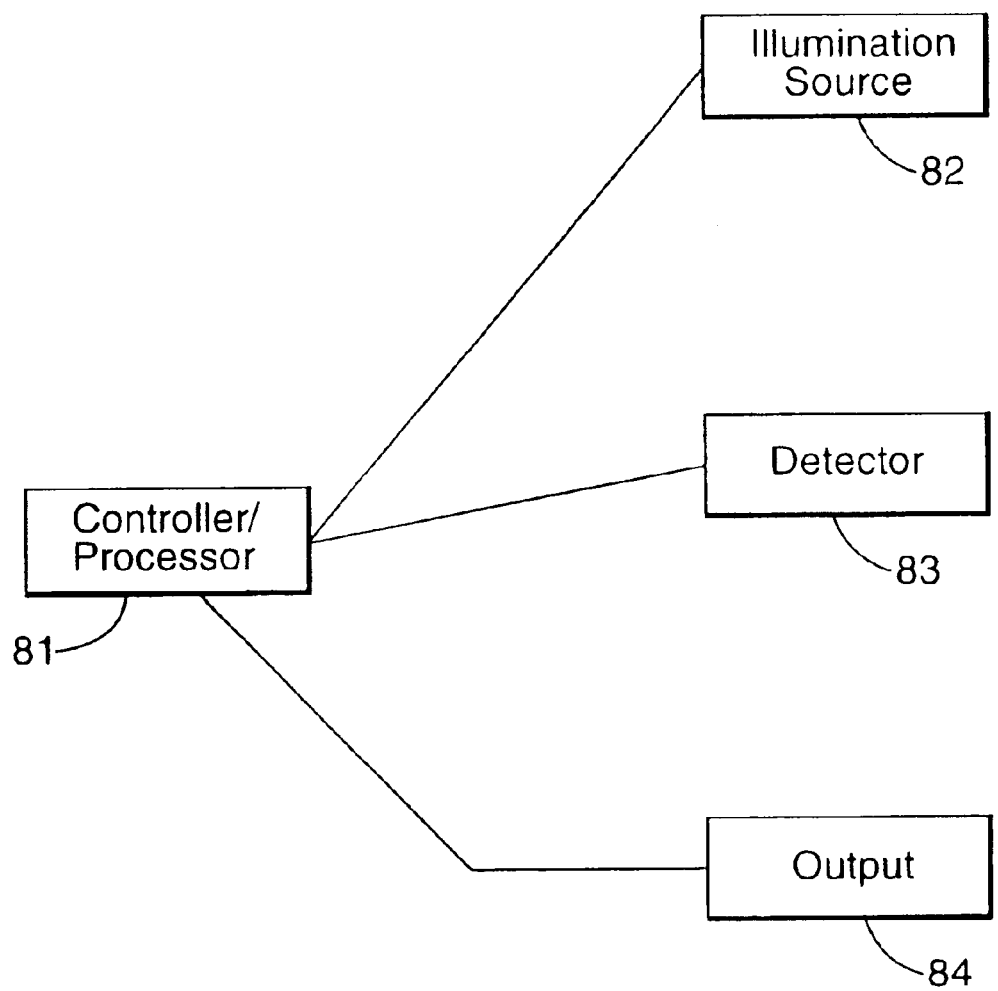
FIG. 17 is a schematic illustration showing components of a reader for use in conjunction with the present invention.

FIG. 17 schematically illustrates components of a preferred embodiment of scanning means according to the present invention. The scanning means comprises an illumination source 82, a controller/processor 81, a detector 83 and an output component 84.

The illumination source 82 may provide any suitable source of energy such as radiation, light or other suitable beam. The detector detects energy reflected from the sterilization indicator 10.

The output component 84 may be any suitable means known in the art including but not limited to display lights, computer displays, graphical user interfaces or further communication to additional electronic hardware.

The controller/processor 81 receives information from the detector 83 and optionally the output component 84. The controller/processor 81 is capable of controlling the components of the scanning means. If the scanning means is a code reader, the processor 81 is capable of reading and decoding the code of the sterilization indicator 10. If the sterilization indicator 10 does not include a code, the scanning means should be capable of distinguishing the appearance of the sterilization indicator 10 before and after it is subjected to a sterilization process in sterilizer 20.

The scanning means for use with the present invention includes code readers and even specially adapted non-code readers. Code readers for reading bar or matrix codes include contact and non-contact fixed beam scanners, moving beam scanners, handheld scanners, fixed mount scanners, and laser and solid state imagers such as charge-coupled devices.

A scanning means comprising a laser scanner may include a visible laser diode for emitting a laser beam, a scanning element (e.g. an oscillating mirror for sweeping the laser beam in a horizontal and/or raster like pattern across the bar code), and receiving optics including a photosensor for sensing the light reflected off the target bar code and converting the light energy into an analog electrical signal, the amplitude of which corresponds to the reflectivity of the target bar code. The device reads the analog signal by processing it, digitizing it and decoding it into data representative of the data that had been encoded into the target bar code. The scanning means is preferably one that is capable or reading and decoding the coded information from the sterilization indicator 10.

In yet another embodiment, the scanning means may comprise a charge coupled reader. A charge-coupled bar code reader can be a one-dimensional or two-dimensional device. A one-dimensional device uses a linear array of photosensors to acquire an image of the cross-section of the entire linear bar code at once. The device produces an analog waveform whose amplitude mimics the darkness and lightness of the bars and spaces of the captured image. Electric charge stored in each of the elements of the charge-coupled device array as a function of the amount of light sensed by an area covered by each element is shifted out serially to form electric signals for processing, digitizing and decoding. Two-dimensional devices function in a similar fashion to capture the entire image of a two-dimensional bar code symbol at once.

The code readers and scanning means associated with the present invention may also comprise any of the reading devices disclosed in Greene, *Production and Inventory Control Handbook*, $3^{rd}$ Edition, McGraw-Hill, New York, (1997), and Longe et al., *Bar Code Technology in Health Care: A Tool For Enhancing Quality, Productivity and Cost Management*, Advanstar Communications, ISBN 0-929870-20-4, Library of Congress Catalog Card No. 93-71570 (1993) (the entire contents of each of which are herein incorporated by reference).

In yet another embodiment of the present invention, the scanning means comprises a densitometer. Typically, a densitometer includes a filter to selectively read and enhance desired colors. To decode the information in a bar code, a small spot of light is passed over the bars and spaces via a scanning device. The bar code will reflect light back into the scanner in various amounts after passing through a filter. The filter could be chosen with preference given to the second color of the identifying indicia used in an automatic reading system of the present invention. As a result, the contrast can be enhanced, thereby improving readability of the bar coded data. The differences in reflections are translated into electrical signals by a light detector in the scanner. This type of reading device may be particularly preferred where the bar code 14 is comprised entirely of a sterilizing agent sensitive ink that changes from one color (e.g. purple) to another color (e.g. green).

It has been found that the surface reflectivity of some steam sterilization sensitive inks varies greatly, even for the same type of ink. For example, the gloss of a particular ink can vary from lot to lot. Top coatings on chemical indicators often have the effect of scattering incident light making an automatic reading of the chemical indicator more difficult. It has been determined that the angle between the illumination source of the scanning means and the sterilization indicator ink influences the character of the reflection from the sterilization indicator ink. General chromatic insensitivity of some conventional barcode readers make them less appropriate for reading some chemical indicators.

Figure 15:
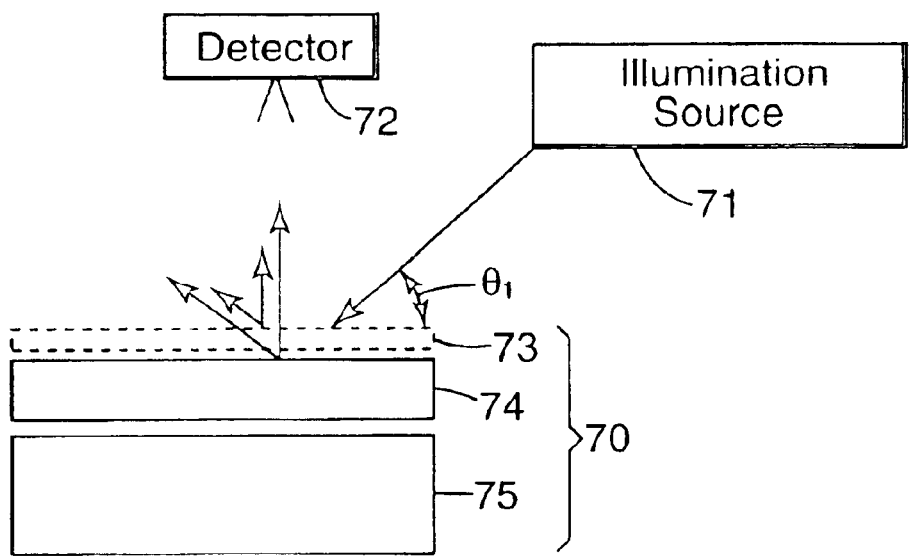
FIG. 15 is a schematic illustration of the test set up used to acquire the graphs of FIGS. 7, 9, 11 and 13.

FIG. 15 is a schematic illustration of a scanning means used to scan a chemical indicator 70. A chemical indicator includes a backing 75, a sterilant sensitive ink coating 74 and an optional top coating 73. The scanning means includes illumination source 71 and detector 72.

The illumination source 71 directs energy toward the surface of the chemical indicator 70. The detector 72 collects energy reflected from the surface. The illumination source 71 preferably provides light at an angle (theta 1) of incidence with the surface. The angle theta one (FIG. 15) is preferably more than approximately ten degrees and less than ninety degrees in order to improve the character of the reflectance from the chemical indicator 70.

Figure 16:
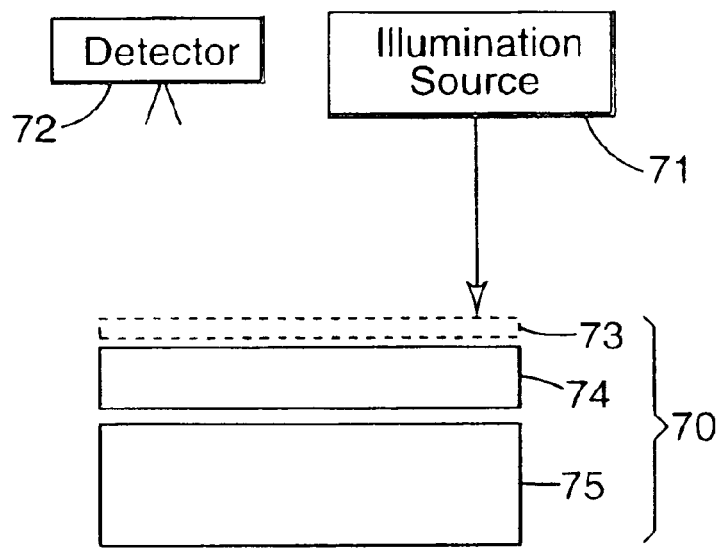
FIG. 16 is a schematic illustration of the test set up used to acquire the graphs of FIGS. 6, 8, 10 and 12.

FIG. 16 illustrates an arrangement where the illumination source 71 provides light at an angle normal to the surface of the chemical indicator 70. This is not a preferred arrangement of the illumination source 71, chemical indicator 70 and detector 72 as the character of the reflection from the chemical indicator 70 is often quite poor, especially when the chemical indicator 70 has a glossy top coat 73.

Preferably, the scanning means of the present invention includes a positioning means for positioning the surface of the chemical indicator 70 relative to the illumination source 71 and the detector 72. This helps control the quality of the reflected light from the chemical indicator 70. The positioning means may comprise a guide, framework or an automatic feeding device such as those found in office copiers. Optionally, the sterilization indicator (e.g. 10) could have positioning indicia or a symbol printed thereon that the reader is programmed to seek in order to properly position the illumination source 71, detector 72 and the chemical indicator. The illumination source 71 and detector 72 could also be made movable relative to the framework of the reader to help ensure proper orientation.

Figure 18:
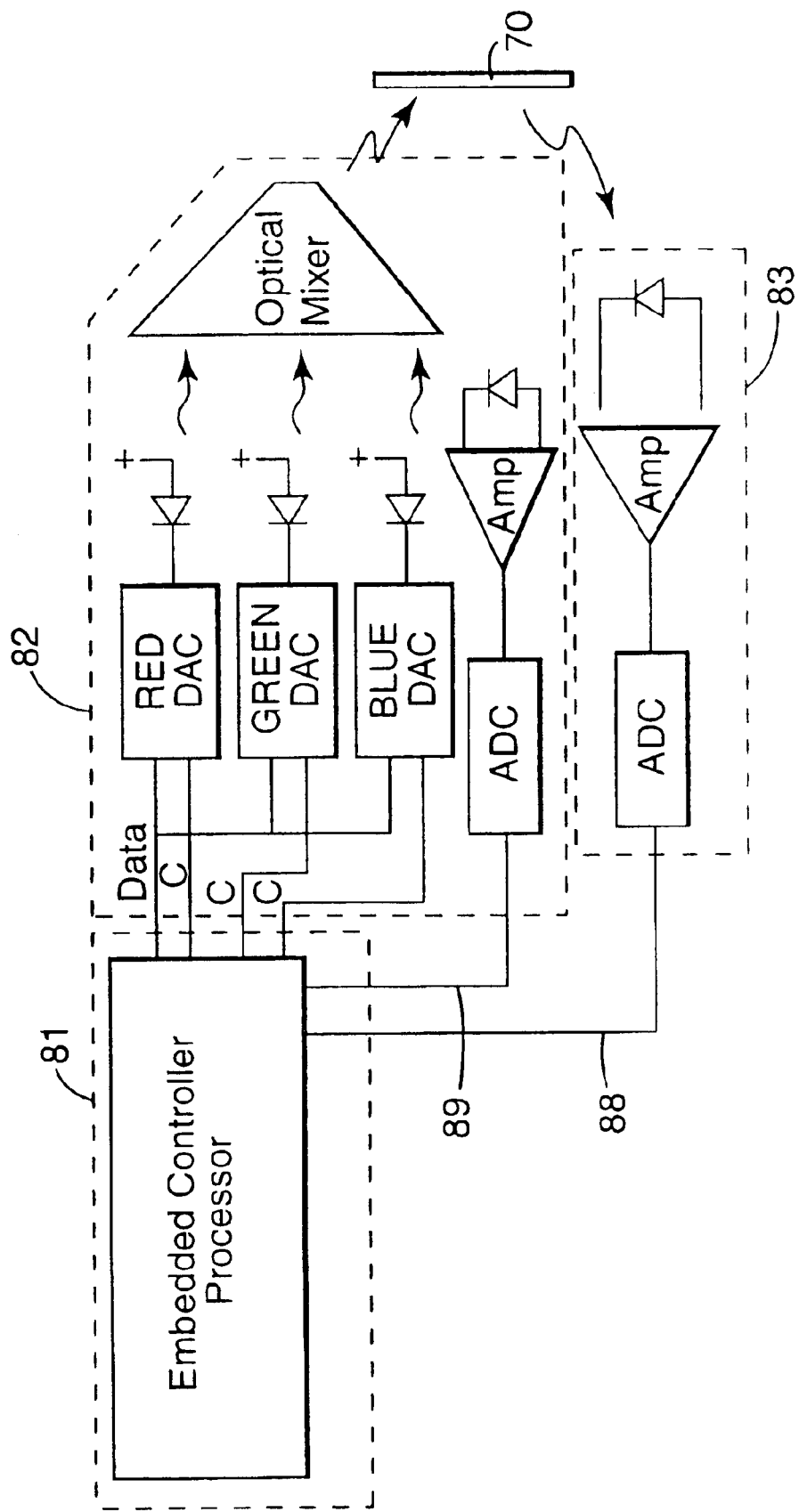
FIG. 18 is a schematic illustration of one embodiment of the components of the reader of FIG. 17.

FIG. 18 is a detailed block diagram of one embodiment of the scanning means of FIG. 17. The device is particularly suitable for reading and interpreting colormetric chemical indicators 10 that do not include sterilization ink in a code form. As discussed above, the apparatus may be described as having generally three components, illuminator 82, detector 83, and controller 81.

In a preferred embodiment, the illuminator 82 has three sources of light, preferably light emitting diodes. Red, green and blue diodes are shown. The current of each diode is set by the controller 81 through the use of a digital to analog converter. The three sources couple light into an optical mixer (waveguide) where the three primary emissions are homogenized and delivered to the chemical indicator 70. A portion of the light may optionally be fed back to a broadband detector 83, which allows closed loop servo control of the sources. The controller 81 receives information from the illumination source 82 and detector 83 via lines 88 and 89. Preferably, the illumination source 82 is capable of scanning through a variety of wavelengths of light. Also preferably, the detector 83 is sensitive in a substantially repeatable fashion to a variety of light sources.

Light from the exit aperture of the waveguide is allowed to interact with the sterilization indicator under scrutiny 70 and is collected by the detector 83.

The controller 81 sweeps through an appropriate spectrum of light by modulating the three color sources. At each significant composite wavelength the controller quantifies the output from the detector 83. Sample points may be predetermined as a function of the model chemical indicator 70 that is being scanned.

Figure 19:
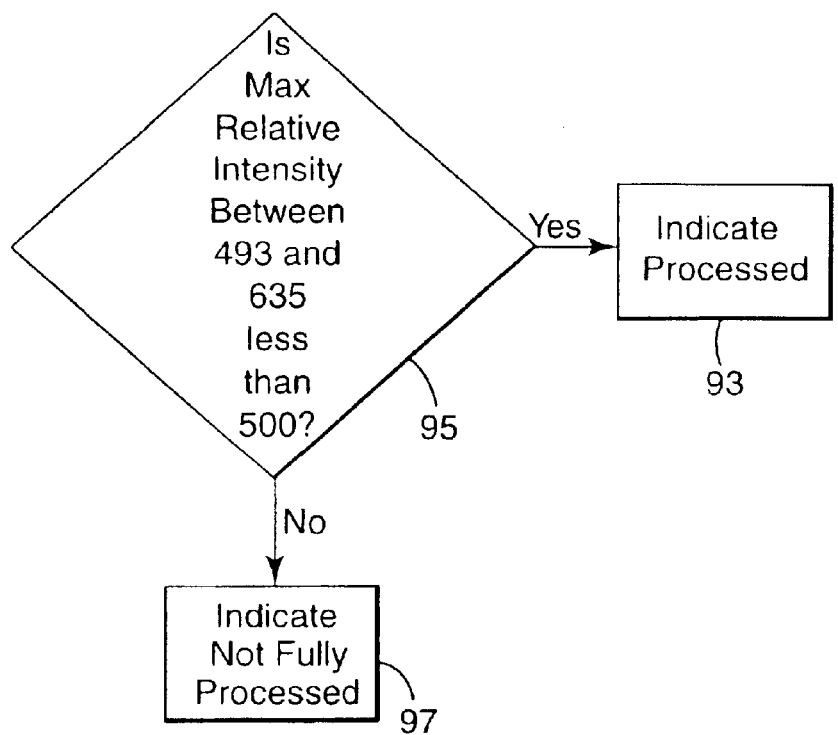
FIG. 19 is a flowchart showing one example of the logic associated with the processor of FIG. 18.
Figure 20:
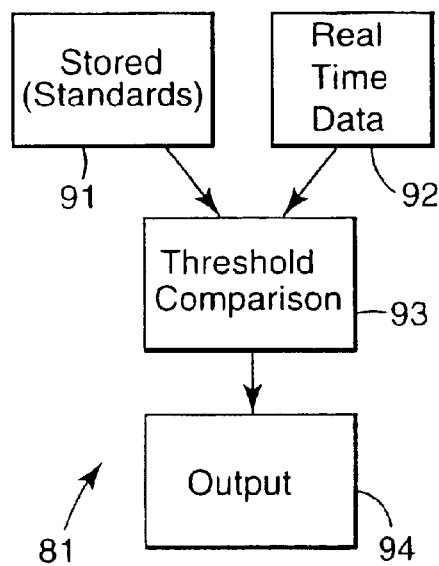
FIG. 20 is a schematic drawing showing the elements of another example of a processor component of a reader according to the present invention.

FIGS. 19 and 20 are examples of embodiments of a processor/controller 81. In FIG. 20, upon spectrally scanning the chemical indicator 70 under scrutiny (see FIG. 20), the processor 81 stores the data 92 from the indicator 70. Typical spectral curve data 91 for the type of indicator under scrutiny may be included in the a storage means (e.g. non-volatile memory) of the processor 81. The data 92 from the indicator 70 may be compared against the spectral curve data 91 from that type of sterilization indicator (e.g. the information that was previously loaded into non-volatile memory). Thresholding 93 may be accomplished by comparing for best matches with known spectral curve data 91. Visual output 94 is rendered to the user. Alternatively, the processor/controller could use logic as shown in FIG. 19 (discussed in greater detail below relative to Example 6).

As discussed above, the processing means 81 can optionally include non-volatile memory that includes reference data. The reference data may include data generated from sterilization indicators that have been exposed to varying degrees of a sterilization process. Various spectral curves may be generated for chemical indicators exposed to different levels of a sterilization process. As another feature, various spectral curves may be generated for chemical indicators subjected to sterilization cycles suffering from common sterilizer failure modes. Spectral tolerancing and limits bands may be established to compensate for production variations for a particular type of chemical indicator. These established spectral curves for a particular type of sterilization indicator may be downloaded into the nonvolatile memory of the reader or scanning means at the time of manufacture or could be otherwise included in a computer means. As new types of chemical indicators become available, the new spectral curves and model numbers may be downloaded to the scanning means/reader/computer.

In this embodiment, the processing means 81 includes means for comparing information generated from the chemical indicator 70 with reference data The reference data may comprise reference spectral curves for the particular type of chemical indicator. For example, if the scanning means is attempting to read a 3M Comply (SteriGage) Steam Chemical Integrator No. 1243A, it can be programmed to open a reference file containing information taken from reference indicators that were subjected to varying degrees of a sterilization process and/or a lethal sterilization cycle and/or a sterilization process exhibiting a known sterilizer failure mode. For example, to construct the reference file, several 3M Comply (SteriGage) Steam Chemical Integrators may be subjected to partial steam cycles that satisfy only two of the three critical parameters of a steam sterilization cycle (e.g. time, temperature and steam). This reference data can be used to assist the scanning means in identifying 3M Comply (SteriGage) Steam Chemical Integrators that indicate that an inadequate sterilization cycle occured.

After scanning the chemical indicator 70 under scrutiny to create a spectral curve, the scanning means may compare this scan against the file with the reference spectral curves for the particular type of chemical indicator. In the nonvolatile memory file, there will be a plurality of reference curves, which may be correlated to a specific sterilant exposure level or particular failure mode as discussed above.

The processing means may optionally include means for determining the character of the sterilization process. For example, the scanning means may compare the curve generated from the chemical indicator under scrutiny and curves in the non-volatile memory and determine the best match. Optionally, the scanning means may assign a sterilant exposure value to the curve generated from the chemical indicator 70 under scrutiny. This value may be compared against a pass/fail threshold. Appropriate information may then be indicated to a user.

The present invention is particularly suitable for use in an integrated electronic record keeping and sterilization monitoring system. Such a system can track medical supplies and devices throughout their life cycle and can monitor the state (e.g. sterilized or contaminated) of such supplies and devices.

The present invention includes a method of monitoring articles to be subjected to a sterilization process. The method includes the steps of providing a sterilization indicator capable of providing information relating to the efficacy of a sterilization process, an article to be subjected to the sterilization process, a reading device capable of obtaining information from the sterilization indicator, and computer means for processing information associated with the sterilization indicator and the article. The method also includes the steps of subjecting the sterilization indicator and the article to the sterilization process, reading information from the sterilization indicator with the reading device and associating information from the sterilization indicator with the article by the computer means. Another aspect of the present invention comprises a system of components (e.g. hardware and software) for use in an integrated sterilization monitoring and inventory tracking system.

Figure 3:
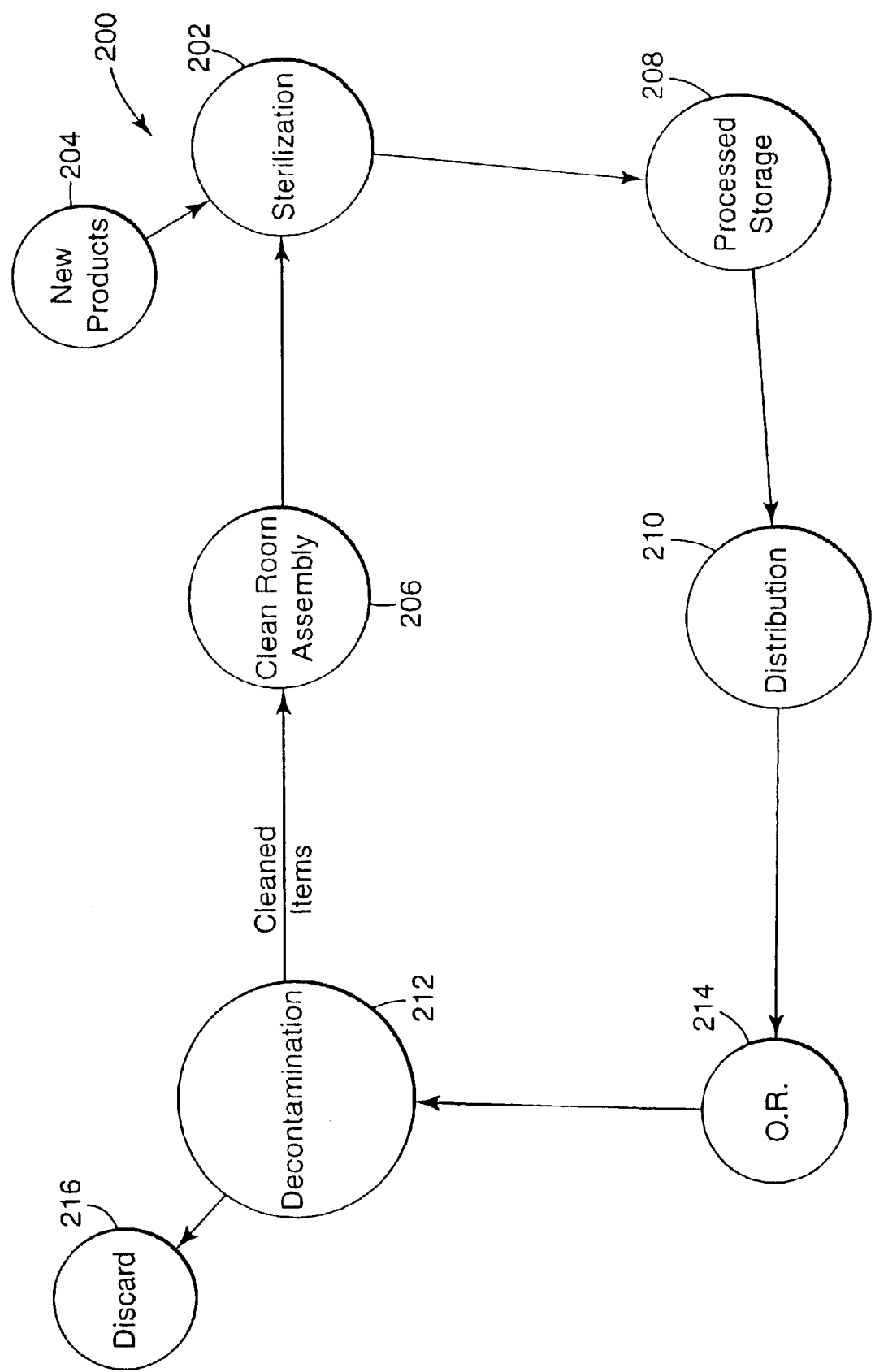
FIG. 3 is a block diagram of an example of a healthcare facility's sterilization assurance system.

FIG. 3 is a schematic view of a sterile processing system 200 in use in a hospital. New products 204 often need sterilization prior to use. Most large hospitals have a central sterilization processing station 202. The central sterilization station 202 often includes several different types of sterilizers (e.g. steam and ethylene oxide). For example, new products 204 or heat sensitive articles can be sterilized within their packaging by an ethylene oxide sterilizer. Alternatively, several initially unpackaged articles can be collected and wrapped with opaque sterilization wrap to create what is known as a pack (e.g. see 12 in FIG. 2). The sterilization wrap is usually secured with indicator tape. Hospitals often place a chemical indicator within a pack as part of its sterilization monitoring procedures. Because the sterilization wrap is opaque, the chemical indicator within the pack cannot be read until the seal provided by the packing material is broken. However, once the seal is broken, the articles within the pack are no longer considered sterile. Thus, sterilization wrap packs are not usually opened until they are placed in the operating room. Once an article is sterilized, it is moved to processed storage 208 to await its use.

Distribution 210 draws processed medical articles from storage 208 and organizes them for use. For example, a kit for a particular type of surgical procedure may be assembled. The kit containing the sterile articles is then sent and used in the operating room 214. If a pack is opened in the operating room 214 and the chemical indicator shows a sterilization failure, delays and other undesirable consequences can result.

Once used, the formerly sterile articles are sent to decontamination 212. From decontamination 212, items are either discarded 216 or, if the device is reusable, the device may be sent to a clean room assembly 206. Once cleaned, the article can be sterilized again at central sterilization 202.

Figure 4:
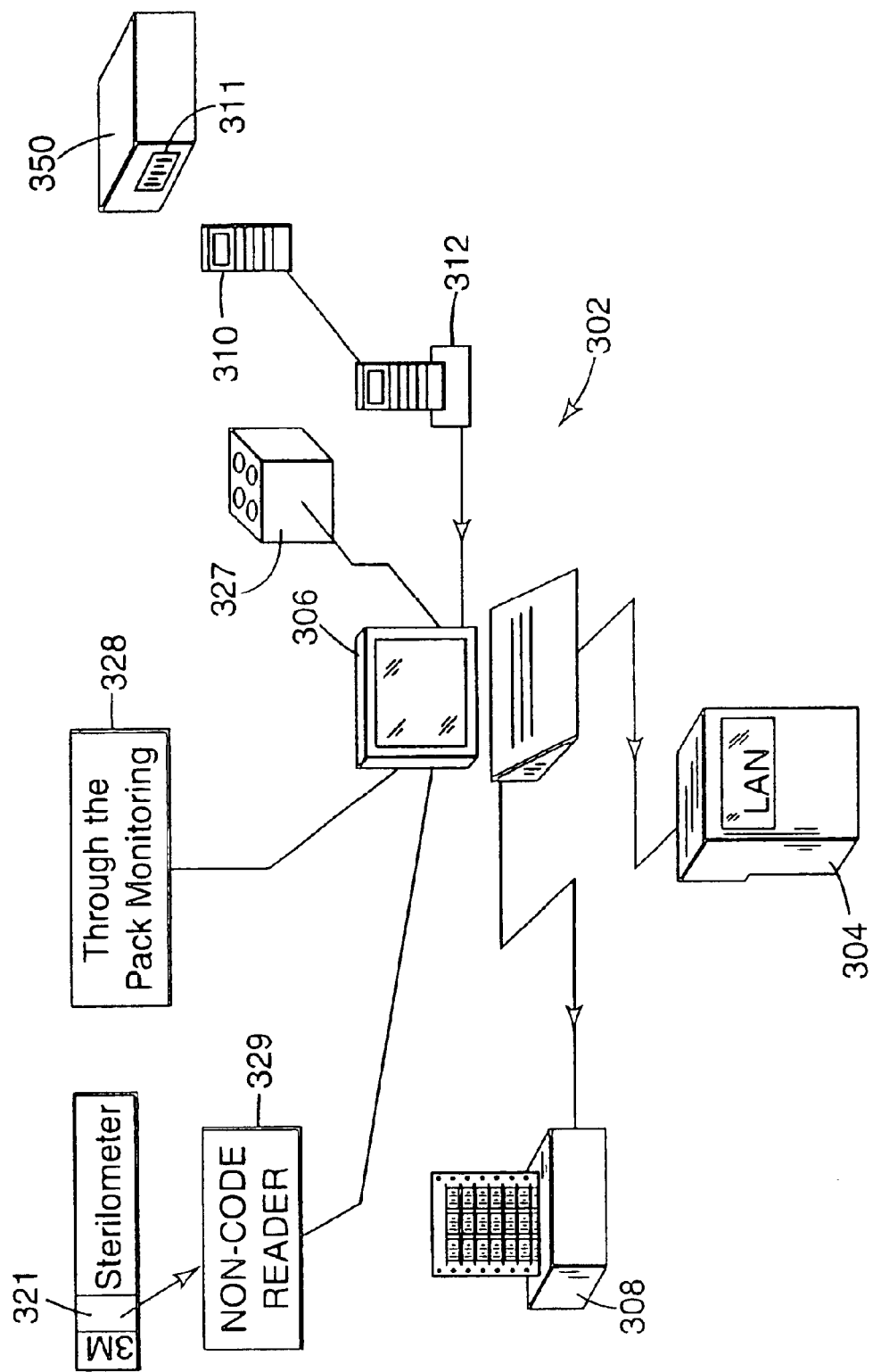
FIG. 4 is a schematic diagram of an integrated electronic article tracking and sterilization assurance system according to one aspect the present invention showing a personal computer, an optional mainframe or central computer, printer; scanning means, hardware for transmitting sterilization assurance information and objects to be scanned.

FIG. 4 illustrates electronic components and architecture of an article tracking system for use with the present invention. The system can be used in an integrated sterilization information and inventory system. The system includes a personal computer 306, an optional mainframe or central computer 304, software, printer 308, and a scanning means such as a bar code reader 312. The bar code reader preferably utilizes a hand held bar code reader 310 that can be separated from the base unit. The system may optionally include electronic connection to a reader 329 for a chemical indicator that includes sterilization sensitive ink in non-code form 321, an automatic biological indicator reader 327 and hardware 328 for reading a sterilization indicator through an opaque pack wrap.

As shown by lines in FIG. 4, the various components of the system may be placed in communication (e.g. electronic communication) by means such as electronic wiring, wireless connections, internet or intranet connections, and/or ethernet connections.

The article tracking system affords the health care practitioner the opportunity to input, monitor and store information about any device or supply used within health care including information: a) provided by manufacturers such as manufacturing dates, lots, regulatory information, shipping requirements, storage requirements, use and reuse conditions and contraindications; b) added during distribution such as actual shipping and storage profiles, c) added within the health care institution including assignment of patient charge codes, inventory codes, department codes, frequency of product use, date of product use and identification of practitioner actually using or prescribing the item, d) retrieved from other devices such as electronic sterilization test packs, electronic sterilization integrators, electronic signals from biological indicator readers 327, electronic signals from bar code readers 312, and link components from multiple sources in a format reflective of how the devices are actually used, and e) that previously could only be read at one location (e.g. the location of a sterilization indicator) but which can now be read simultaneously at several locations, even remote locations. As a result, the system improves inventory management, cost management, reimbursement management, patient record management, and security management at the health care site.

Information from a device 327 for automatically reading the results of a biological indicator can optionally be connected to the computer 306 as a part of the system. U.S. Pat. Nos. 5,030,832; 5,063,297; 5,334,841 and 5,863,790 and U.S. patent application Ser. No. 08/856,104, filed May 14, 1997 and 08/967,747 filed Nov. 10, 1997 (the entire contents of each of which are herein incorporated by reference) describe electronic reading apparatus for objectively reading fluorescence of biological indicators. These devices can be modified to provide information to the system of the present invention.

Unlike prior art systems, information from the reader 327 can be fed directly to computer 306 without the need for a user to manually type the results of the biological indicator into a sterilization monitoring or inventory system. The chance for human error in the system is thereby reduced.

Figure 31:
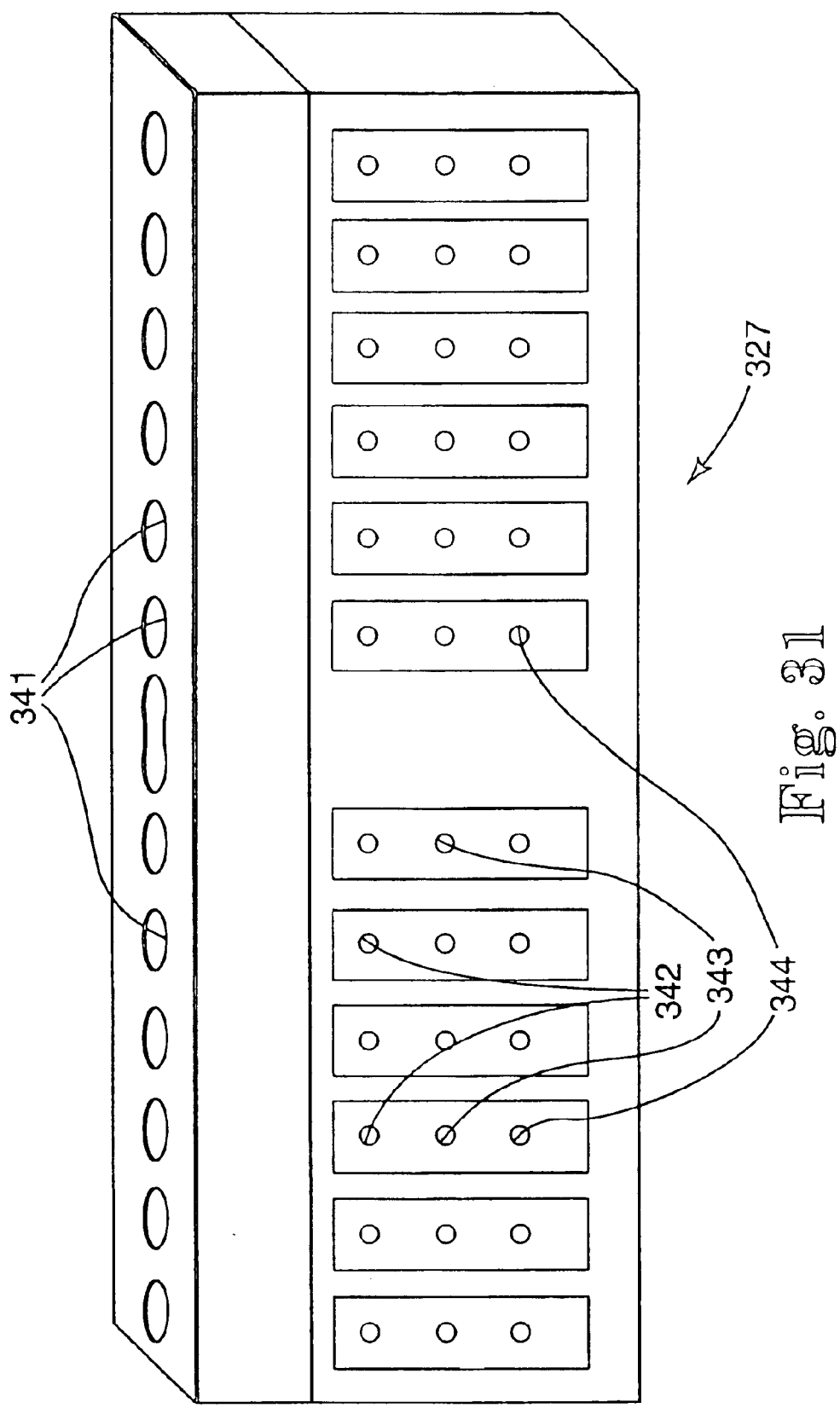
FIG. 31 is a view of a computer screen showing an example of a screen for use with a device for automatically reading the results of a biological indicator.

FIG. 31 illustrates a simulated computer screen or graphical user interface for the device 327 for automatically reading the results of a biological indicator. The device 327 may include a plurality of wells 341 for receiving biological indicators, electro-optical components for reading the biological indicators and output components for sending information relating to the biological indicators to a user. The output components may include a series of three lights for each biological indicator. A first light 342 may indicate whether a biological indicator is properly seated in the corresponding well 341. A second light 343 may indicate that the biological indicator within the corresponding well indicates a failed sterilization cycle. A third light 344 may indicate that the biological indicator within the corresponding well indicates a lethal sterilization cycle. Optionally, the article tracking system (see FIG. 4) of the present invention can receive electronic information directly from the electronic biological indicator reader 327. Thus, the information from the biological indicator can be directly entered into the article tracking system merely by having the user operate the reader 327. There is no need to have the user take further steps to associate information from the reader 327 with the articles that were sterilized with the biological indicator.

The system may optionally include a reader 328 that is capable of reading a sterilization indicator within an opaque pack. U.S. Pat. Nos. 4,850,716 and 5,745,039 describe devices capable of reading a sterilization indicator within a pack without the need for opening the pack. As shown in FIG. 4, information from the through-the-pack reader 328 can be electronically supplied to computer 306. The user simply machine reads the sterilization indicator with the reader 328 and the sterilization information is automatically fed to computer 306 without additional opportunity for user recordation error. Early indication of sterilizer failure is particularly helpful in that it reduces the chances that a pack 350 with non-sterile contents will enter the carefully prepared and maintained sterile field found in the operating room 214 (FIG. 3).

FIGS. 21 through 30 are examples of computer screens that might be utilized in one embodiment of sterilization monitoring tracking system according to one aspect of the present invention. The computer can be programmed to grant a user access to information relating to the status of articles in the sterilization system of a hospital (see FIG. 3). It can also be linked to other databases used at the hospital including surgical demand and inventory management databases. As discussed in more detail below, the computer program can also be used to customize chemical indicators to suit the particular needs of the hospital.

Figure 21:
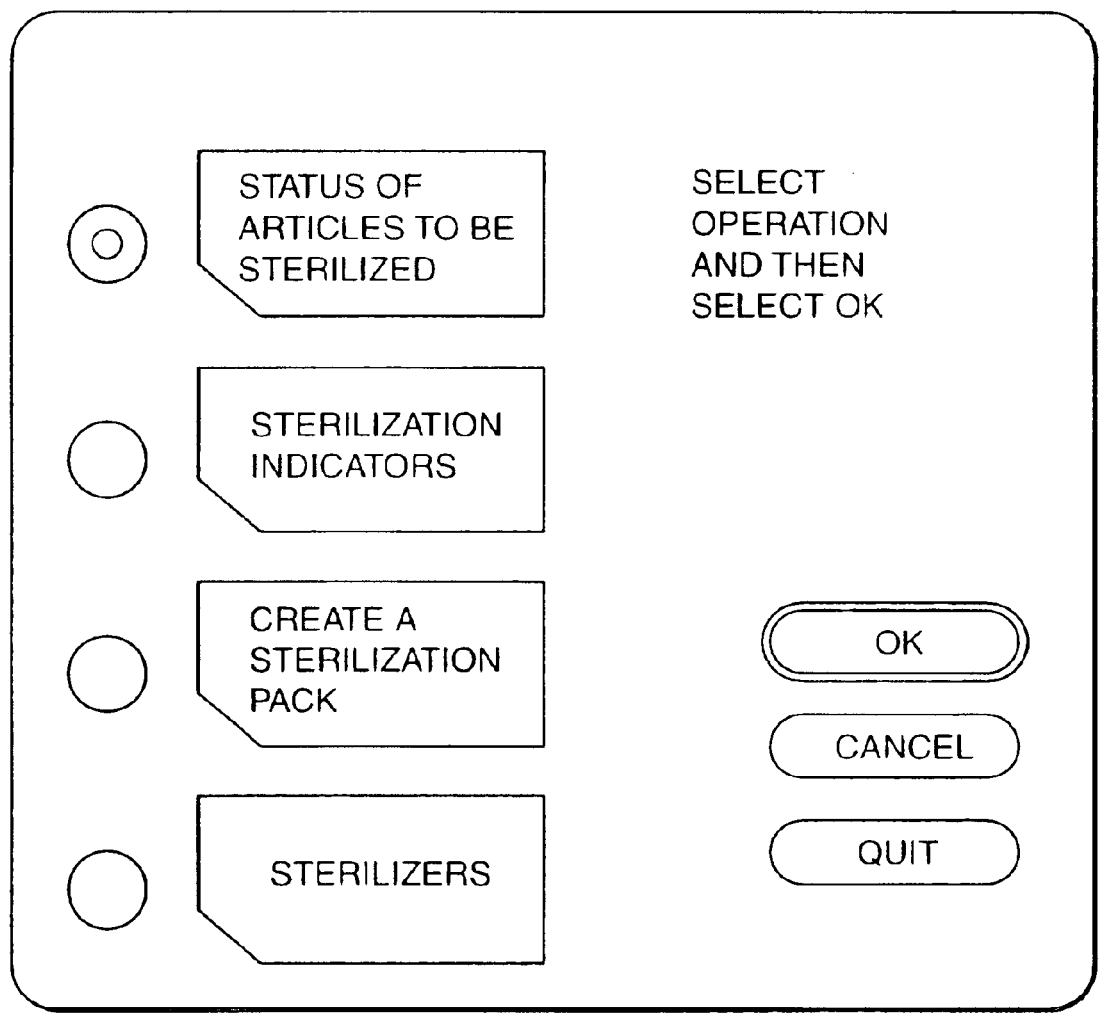
FIG. 21 is a view of a computer screen of an example of a sterilization monitoring tracking system according to an aspect of the present invention.

FIG. 21 is an example of a computer screen of a graphic user interface for a total sterilization management system. The user can select from various options to obtain information relating to the sterilization monitoring activities of a health care facility. In the embodiment of the present invention shown in FIG. 21, the user could choose to manage or use information relating to the status of articles to be sterilized, such as the location or sterilization state (e.g. processed or unprocessed) of such articles. Alternatively, the user could choose to obtain information concerning sterilization indicators or the sterilizers themselves. Finally, the user could choose information concerning the contents or construction of a sterilization indicator, such as instructions relating to the creation of a sterilization pack.

Figure 22:
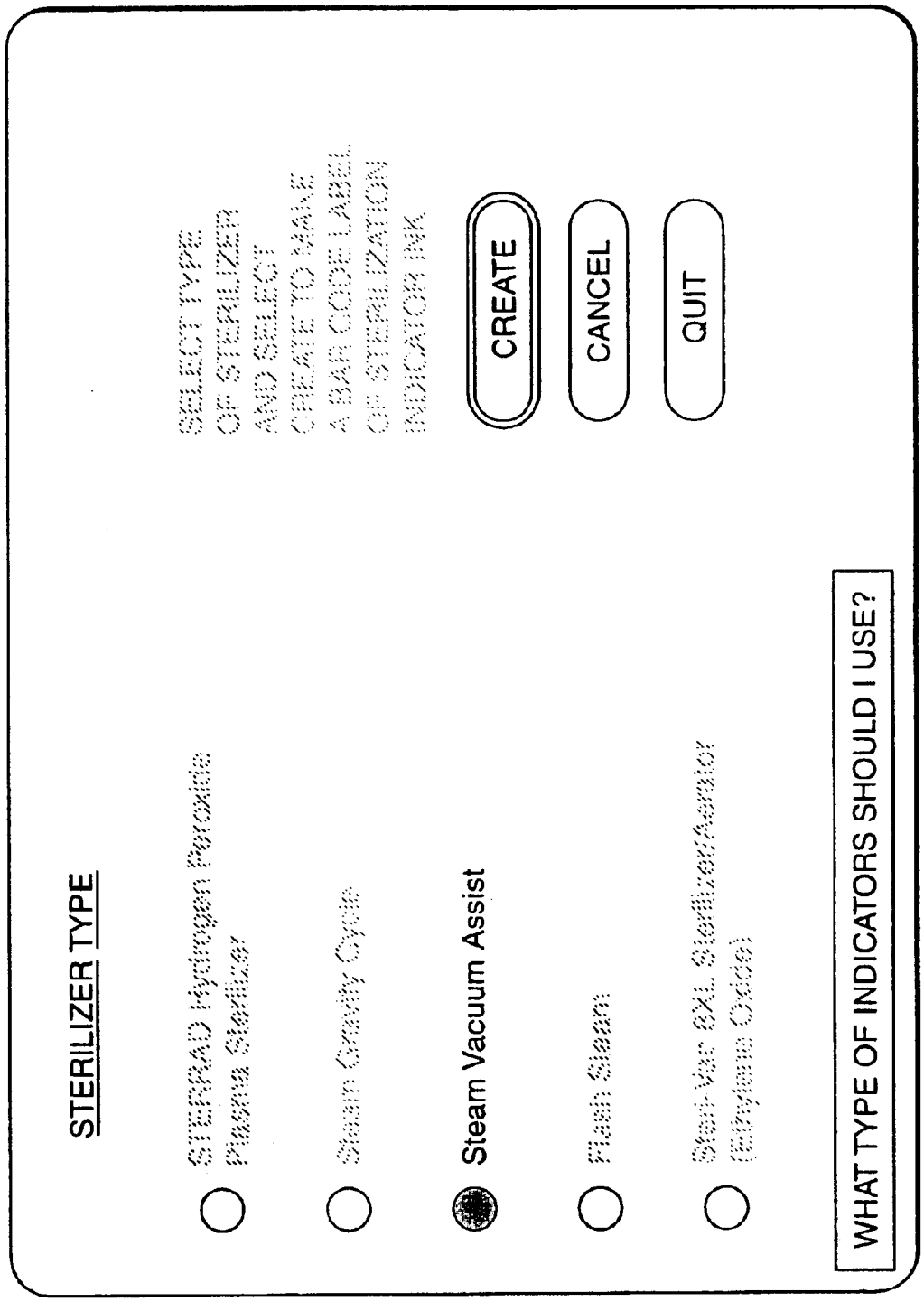
FIG. 22 is a view of a computer screen of the sterilization monitoring tracking system of FIG. 21 after "sterilizers" has been selected.

FIG. 22 is an example of a computer screen of a graphic user interface that a user could encounter after selecting "sterilizers" in FIG. 21. At this point, a user could select information relating to suggested sterilization indicators for use in the particular sterilization cycles selected. Alternatively, the user could choose to construct his or her own customized chemical indicator for the preselected sterilizer. Optionally, a user could obtain additional information concerning the preselected sterilizer such as proper loading instructions, loading density, and contraindications. As an example, a particular sterilizer may not be approved by a regulatory agency for sterilization of certain articles (e.g. surgical instruments with a lumen). The system may be designed to encourage uses of the sterilizer consistent with approved uses. It may even include means for preventing use of the sterilizer outside its approved uses.

There is a position in the sterilization chamber of some sterilizers that is known to be the most difficult point to sterilize. For some sterilizers, it might be near a drain, for other sterilizers, it may be another location. Many regulatory guidelines call for a sterilization indicator to be placed in the position in the sterilization chamber that is known to be the most difficult position to sterilize. Once the user selects a particular sterilizer in FIG. 22, the system can optionally provide sterilization indicator placement information to the hospital employee. This could be in the form of an illustration showing the proper position.

Figure 23:
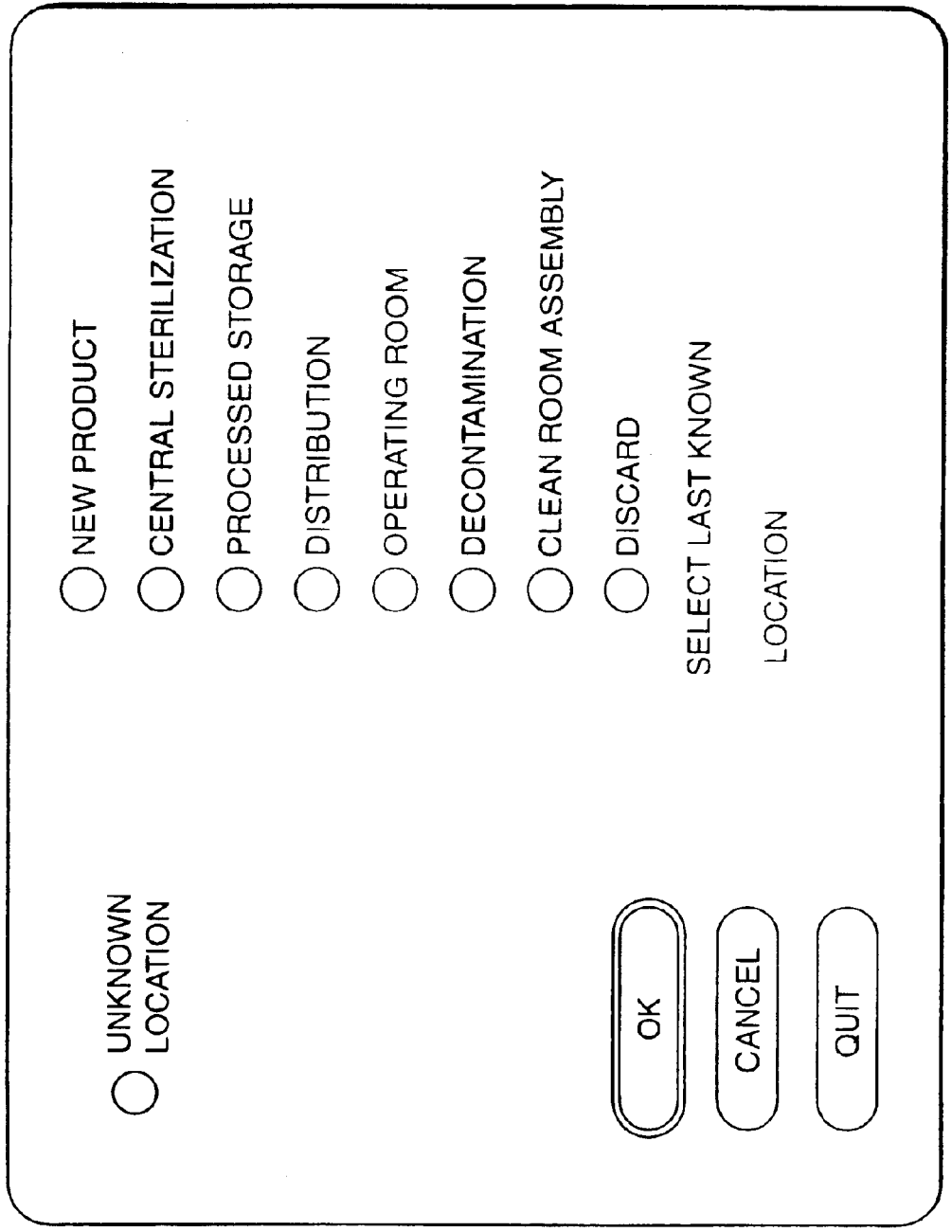
FIG. 23 is a view of a computer screen of the sterilization monitoring tracking system of FIG. 21 after "Status of Articles to be Sterilized" has been selected.

FIG. 23 is a view of an example of a graphic user interface presented on the computer screen after a user selects "Status of Articles to be Sterilized" in FIG. 21. This screen could help a user track an item in the sterilization system of a hospital. For example, a user in a distribution unit 210 of a hospital (FIG. 3). may need to know whether there are any sterile trocars at that location in order to assemble tools for an upcoming sterilization cycle. This screen can help the user find this information and identify its location. As another example, this information could be linked to a surgical demand database for use or exchange of information such as patient names, surgeon names, surgical procedure numbers and surgical procedure types.

FIG. 24 is a view of the graphic user interface screen after a user selects "Sterilization Indicators" in FIG. 21 and a particular type of sterilization procedure (e.g. a steam vacuum assist cycle). This screen assists a user in selecting the most appropriate products for use in the hospital's sterilization monitoring or assurance systems. Optionally, additional information such as training, disposal procedures, set up or recommendation information may be provided. For example, some test packs for ethylene oxide sterilizers require an aeration period prior to disposal. The system according to the present invention may be designed to communicate proper disposal procedures to the user.

Figure 25:
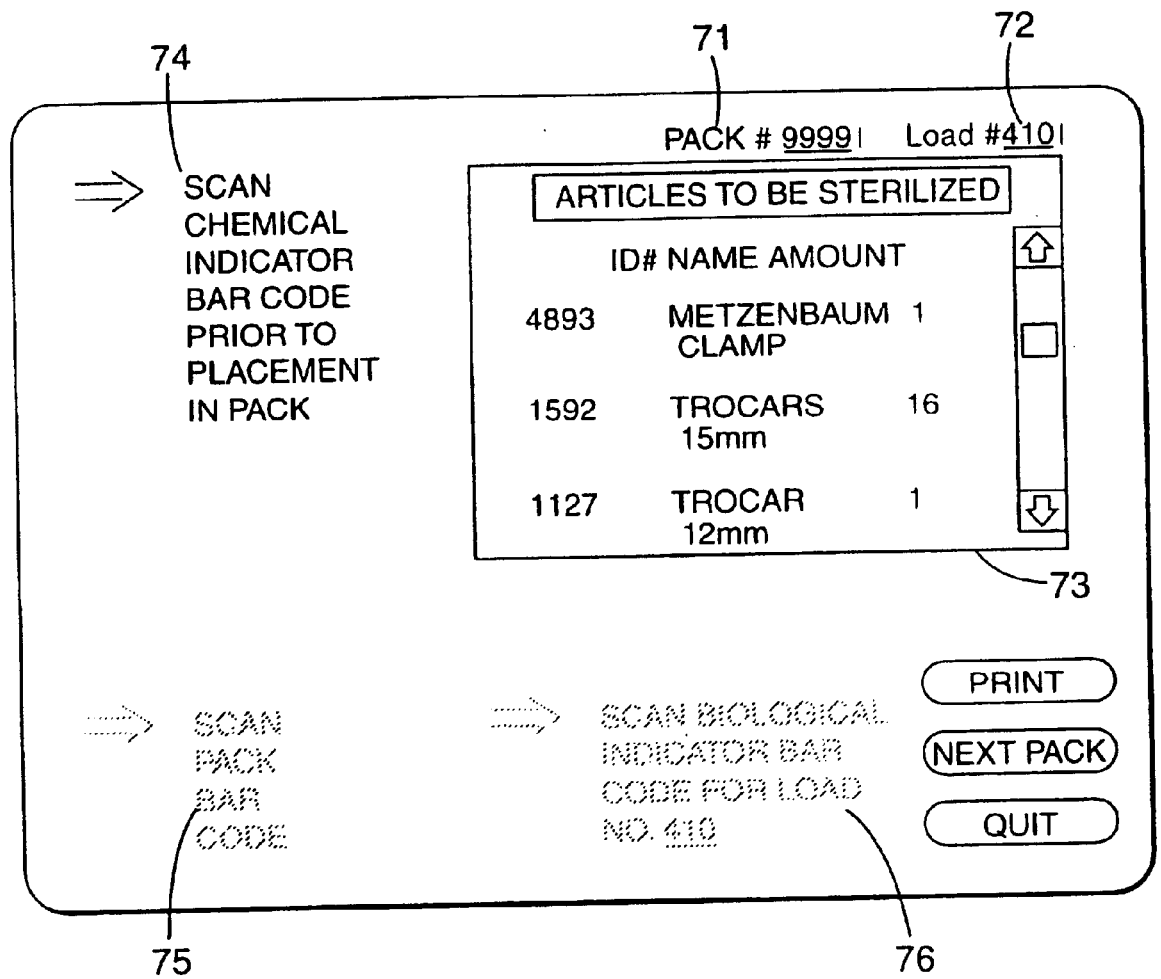
FIG. 25 is a view of a computer screen of a sterilization monitoring tracking system which identifies a particular pack to be subjected to a sterilization procedure, the contents of the pack, and steps to occur during a sterilization monitoring process.

FIG. 25 is a view of the computer screen of a graphic user interface for a sterilization monitoring tracking system which identifies a particular pack to be subjected to a sterilization procedure 71, the contents of the pack 73, a load number, and steps to occur during a sterilization monitoring process 74, 75 and 76. The prompts 74, 75 and 76 can be used to assist the user in properly performing sterilization assurance procedures adopted by a particular hospital. Prompts 74 and 76 can also help correlate information from a sterilization indicator with information relating to the particular items to be sterilized (e.g. the pack contents 73). This information could be readily integrated into the hospital's inventory management database that typically includes information relating to standardized instrument sets, pack numbers, components of packs and set-up instructions. Placing this information in an information management system that includes a local area networking features (LAN) increases access to the information.

FIG. 25 is one example of how sterilization information may be correlated with the actual articles subjected to a sterilization process. In this figure, several articles within pack no. 9999 are identified. For example, a user may manually enter the articles to be subjected to the sterilization cycle (the Metzenbaum clamp or trocars shown in FIG. 25) into the computer database. Alternatively, the article to be subjected to the sterilization cycle may optionally have a bar code associated with it, as described for example, in German Offenlegungsschrift No. DE 3 917 876 A1 or U.S. Pat. No. 5,610,811 (the entire contents of each of which are herein expressly incorporated by reference). That bar code could optionally be read and the information automatically identified to the computer database.

The load for the particular pack is also identified in FIG. 25. Pack number 9999 is designed to be sterilized within a particular load (#410). If the items within pack 9999 should not be sterilized in the predetermined load, the system may optionally provide a warning signal to the user. As an example, if the article to be sterilized cannot withstand the heat of a steam cycle, the system of the present invention can send a warning to the user if load number 410 is to be a steam sterilizer load. As another example, if the sterilizer for a particular load (e.g. load number 410) is not approved for a particular type of article to be sterilized (e.g. a surgical instrument with a lumen such as a trocar), then appropriate information may be sent to the user.

It will be appreciated that there are many different safeguards that could be built into the system. As yet another example, if the particular article to be sterilized needs to be cleaned prior to being subjected to the sterilization cycle, then the system can help ensure that cleaning occurs prior to the article being sent to central sterilization. Referring to FIG. 3, an article in decontamination 212 can be identified as being cleaned or dirty. This information can be stored in the database of the system depicted in FIG. 4. If the status of the article is "dirty", then the system can provide a warning if a user attempts to distribute the item to central sterilization 202 prior to cleaning.

The proper set up and use of packs may be facilitated by the sterilization article tracking system according to the present invention. For example, the system according to the present invention may include illustrations of articles appropriate for the pack or methods of optimally assembling particular items in the pack. This can help avoid packs that are loaded too densely or otherwise loaded in a fashion that would interfere with the sterilization process.

In another aspect of the present invention, the screen shown in FIG. 25 may be designed to prompt a user as to the proper series of steps to take according to the sterilization monitoring procedures adopted by the hospital. It should be noted that the system can be customized to adopt the particular guidelines preferred by the hospital. Virtually any of the guidelines found in JCAH, AORN, ASHCSP, AORN and AAMI can be readily incorporated in the system according to the present invention.

Referring again to FIG. 25, prompts 74 and 75 can link a chemical indicator readout to articles within a sterilizer pack. Prompt 76 can link a biological indicator readout to those same articles. More specific instructions relating to how to create a challenge pack may also be provided to the user.

The system according to the present invention may also be an element of a recall system that helps prevent the use of products that are not sterile. FIG. 26 is an example of a computer screen that issues a warning and provides further instructions to a user. This may be presented to a user if an attempt is made to send an article from a failed sterilization cycle to the operating room for use in a surgical procedure. It can also provide information to central sterilization relating to the performance of a particular sterilizer. Appropriate remedial measures may then be taken by the hospital.

Figure 30:
FIG. 30 is a view of a computer screen showing an example of a screen for use in customization of a chemical indicator.

Referring now to FIGS. 27 and 30, there are shown examples of sample computer screens for graphic user interfaces that may be utilized by a hospital to custom design its own chemical indicators. The computer screen 391 allows a user to custom create his or her own chemical indicator (e.g. for a particular pack) or obtain information relating to sterilization indicator selection for a particular sterilization cycle (e.g. a steam vacuum assist cycle).

FIG. 30 is an example of a screen that may appear if the user selects "create a bar code chemical indicator" (e.g. for a particular pack) in FIG. 27. Alternatively, the user can create his or her own indicator independent of the pack. This allows the hospital (as opposed to the manufacturer of the chemical indicator) to design the information associated with the chemical indicator.

The system depicted in FIGS. 27 and 30 may be readily integrated into a healthcare facility's combined sterilization assurance and inventory system. The graphical user interfaces in FIGS. 27 and 30 are capable of exchanging information between a user and computer means (e.g. personal computer 306 or mainframe 304 shown in FIG. 4).

FIG. 30 illustrates another example of how the system according to the present invention may associate sterilization information with a particular article to be sterilized. As discussed above in relation to FIG. 25, the articles to be sterilized within a pack can be identified to a computer database. The chemical indicator created in FIG. 30 could be a label 410 for placement on a particular pack. The bar code shown in FIG. 30 could optionally be printed from a sterilization sensitive ink. As discussed above, a chemical indicator reader may be designed to read the particular bar code and determine whether it indicates a adequate or inadequate sterilization cycle. Thus, the information relating to whether the sterilization cycle was adequate or inadequate can be directly linked to the articles subjected to the sterilization cycle.

Referring now to FIGS. 4 and 30, the computer (e.g. 304 or 306) preferably stores information relating to at least two types of sterilization procedures (e.g. one of sterilization procedures 401, 402, 403 or 404), at least two different types of sterilization sensitive indicating inks corresponding to the sterilization procedures (e.g. inks for creating a chemical integrator and inks for creating a process indicator), and at least one pattern for printing the inks (e.g. the bar code 405, a rectangular strip 406 or a custom designed shape for the ink 407).

Figure 14:
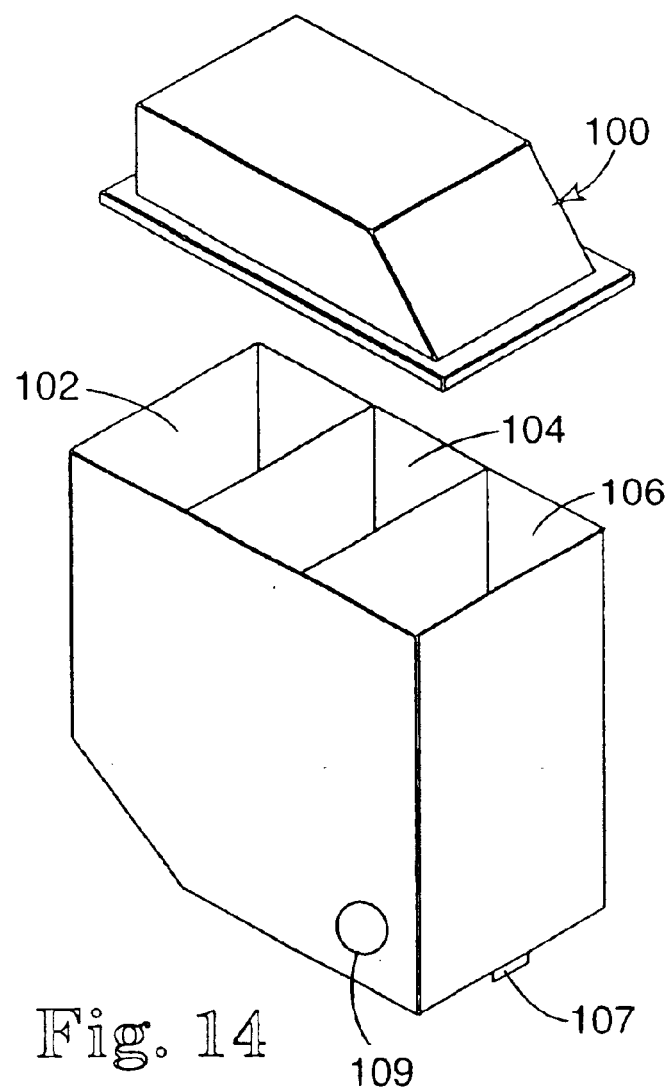
FIG. 14 is a perspective view of an ink jet printer cartridge for use in one aspect of the present invention.

FIG. 14 illustrates an ink jet cartridge 100 for use with a printer 308 that comprises an ink jet printer. The cartridge 100 has three different ink wells 102, 104 and 106 for different types of inks. For example, the ink within well 102 could comprise a colorfast, permanent ink. The ink within well 104 could comprise an ink that is sensitive to a steam sterilization cycle while the ink within well 106 is sensitive to an ethylene oxide sterilization process. The cartridge also includes an orifice 107 for dispensing the ink and a means for selecting ink from the wells 102, 104 and 106.

As shown in FIG. 30, the graphical user interface including means for selecting from information stored in the storage means of the computer. The system also includes printing means (e.g. printer 308, FIG. 4) for printing the chemical indicator on a backing.

For example, the printing means may comprise an ink jet printer 308 with an ink jet cartridge having an ink jet printable, sterilization sensitive indicating ink. Optionally, the system may include backing correlating means 408 for correlating a particular type of backing with a predetermined, compatible sterilization procedure. As depicted, the software could include a feature that automatically selects an appropriate backing for a particular sterilization indicator. Alternatively, the software could simply include a "check substrate" dialogue box or merely a reminder to use a particular printer tray that has been loaded with the appropriate substrate (e.g. tray 1 of the printer is always paper while tray 2 is always polymeric). As another alternative, the printer could include a weight or density sensor to assist in identifying the appropriate backing material for the particular sterilization indicator.

The system also preferably includes ink correlating means for correlating a predetermined sterilization sensitive indicating ink to a sterilization procedure and for preventing the printing means from printing the predetermined ink. As an example shown in FIGS. 4 and 14, the printer 308 and ink jet cartridge 109 may include Hall sensors that can identify the particular type of cartridge 100 placed in the printer 308 to the computer 306 or 304. If the ink jet cartridge 100 does not include an ink within well 102, 104, or 106 that is designed for use with the particular sterilization cycle, the system can prompt the use to replace the cartridge with a cartridge having the appropriate ink. Once the hall sensor means indicates that the printer 308 is loaded with the appropriate cartridge, the user may proceed to print out the sterilization indicator 410.

The advantage of the system shown in FIGS. 27 and 30 is that it creates the chemical indicator at a location close to its actual use. On site data or needs help define the chemical indicator, not the manufacturer. As used herein, when it is said that a sterilization indicator is printed at a healthcare facility, it means that the sterilization indicator is actually completed at a hospital, surgical center, or other facility in which healthcare services are provided, as opposed to it being completed at a manufacturing facility that is substantially dedicated to the manufacture of a sterilization indicator.

FIG. 30 illustrates some information 410 that can be included in the sterilization indicator. This information could be readily modified according to the healthcare facility's actual needs.

FIG. 28 is an example of a computer screen of a graphic user interface of a sterilization monitoring tracking system showing a particular item's sterilization history. This screen is preferred for use in a method of monitoring articles to be subjected to a sterilization process comprising the steps of providing a sterilization indicator (e.g. a chemical or biological indicator) capable of providing information relating to the efficacy of a sterilization process, an article to be subjected to the sterilization process (e.g. a trocar), a reading device (e.g. the bar code reader 312, the non-code reader 329, the autoreader 327 and/or the through-the-pack monitor 328 (described in greater detail below) capable of obtaining information from the sterilization indicator, and computer means (e.g. 306 and/or 304) for managing information associated with the sterilization indicator and the article; subjecting the sterilization indicator and the article to the sterilization process; reading information from the sterilization indicator with the reading device; and associating information from the sterilization indicator with the article by use of the computer means. Unlike prior art systems, the sterilization history of a particular product is automatically recorded and managed and can be displayed, for example, in the fashion shown in FIG. 28. The opportunity for human error is reduced.

It should be noted that the system shown in FIG. 4 is capable of receiving and processing diverse information. For example, with the through the pack monitor, the step of reading information from the sterilization indicator with said reading device includes the step of reading the magnetic property or radio frequency signals of the sterilization indicator. With a chemical indicator scanning means of the present invention, the step of reading information from the sterilization indicator with said reading device may include the step of: reading the infra red emissions from the sterilization indicator. With a biological indicator reader 327 the step of reading information from the sterilization indicator with said reading device includes the step of: reading fluorescence from the sterilization indicator.

Preferably, the computer means 304, 306 is capable of receiving, processing, transmitting, and printing data relating to the article and the sterilization indicator.

Figure 29:
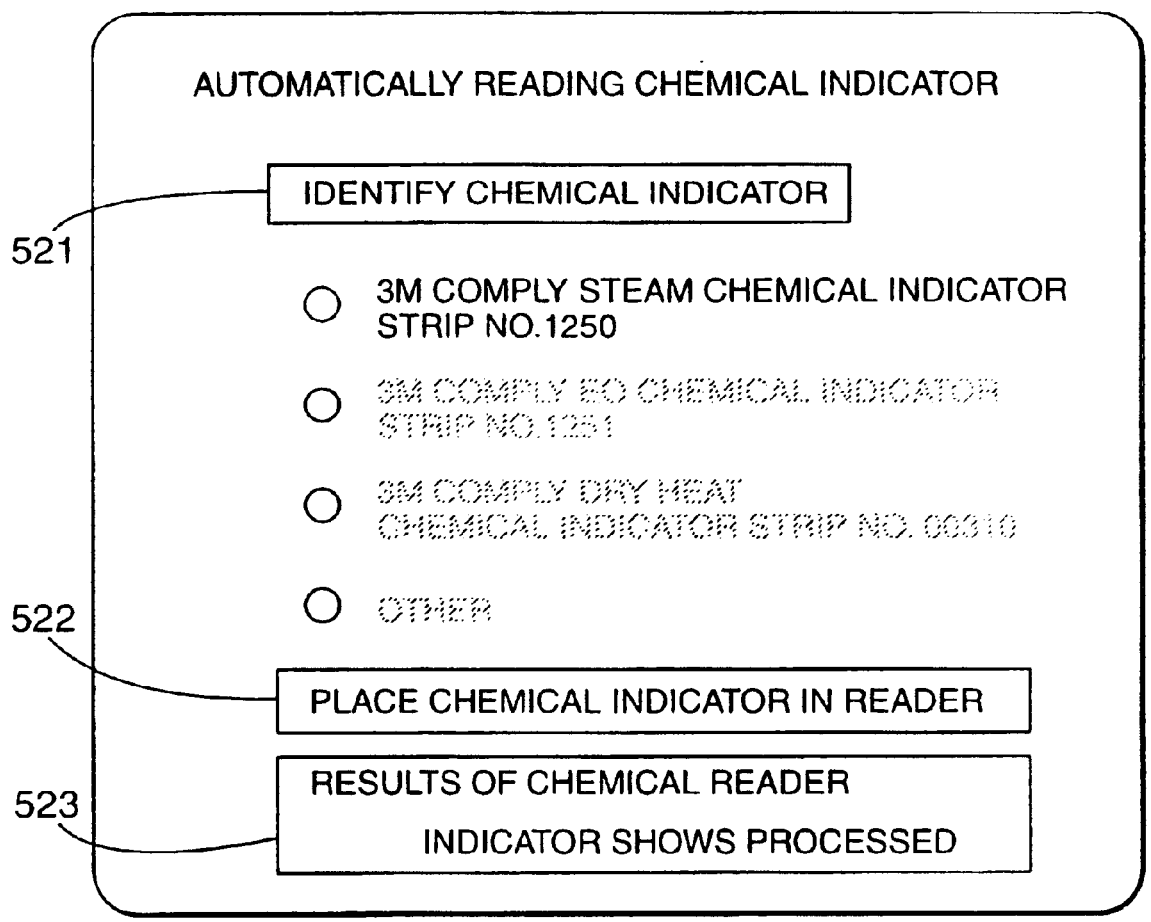
FIG. 29 is a view of a computer screen of a sterilization monitoring tracking system showing steps associated with automatically reading a chemical indicator.

FIG. 29 is a view of a computer screen of a sterilization monitoring tracking system showing steps associated with automatically reading a chemical indicator. The prompts assist a user in properly operating a machine for automatically reading a chemical indicator. The first prompt 521 can provide information to the controller (e.g. 81 of FIG. 17) of the scanning means. The information allows the controller to compare the readout of the chemical indicator with data stored in nonvolatile memory. The next prompt 522 may be used to ensure that the positioning means of the scanning means is operating properly (e.g. the chemical indicator is properly placed relative to the illumination and detection elements of the scanning means). Finally, the scanning means can provide output 523 to the user.

In a preferred embodiment, the system is designed to assist a hospital in complying with recommended practices, guidelines or other procedures designed to meet a sterility assurance level. For example, the CDC Guidelines For Handwashing and Hospital Environmental Control (1985) specify that biological indicators should be used at least once a week and in each load if it includes implantable objects. The system could optionally include a screen designed to remind the user that a biological indicator should be used with a particular load. As another example, the AORN Recommended Practices for Sterilization in the Practice Setting (1997) sets forth that a biological indicator should be used when evaluating sterilization of new items. The system could include a means for identifying new items, and a screen for reminding the user that a biological indicator should be used in that particular load. Optionally, the system could include a means for disabling a sterilizer or preventing its use in the event an operator deviates from the sterilization practices adopted by the hospital.

EXAMPLE 1

Eight gallons of white steam indicator ink were triple roller milled using the composition described in Table 1 a. The ink was screen printed on Monatec 5111-120 paper available from Monadnock Paper Mills, Bennington, Vt. The printed paper was cut to form indicator strips (Run 1) 20.3 centimeters long and 1.6 centimeters wide (8 inches by ⅝ inch) and perforated in the middle. The strips were overcoated using a 390 mesh screen with "UV #600" ultraviolet protector available from Midwest Coatings, Inc., North Kansas City, Mo. The amount of ink deposited after drying was 0.008 grams/square centimeter. Sheets were also screen printed with white steam indicator ink on Type S-14526 paper available from Kimberly Clark, Atlanta, Ga. However the sheets were not overcoated (Run 2).

TABLE 1a

White Steam Indicator Ink Formulation used in Runs 1–2

| Component | | Weight |
|---|---|---|
| Generic Name | Trade Name/Source/Address | (percent) |
| Lead carbonate | Halstab White Lead A/Halstab/ Hammond, IN | 24.88 |
| Sulfur | #21–95/Akronchem/Akron, OH | 08.56 |
| Magnesium Carbonate | 5950/A R Mallinkrodt/St. Louis, MO | 08.32 |
| Lithium Carbonate | Cyclone Fine #400-A/Lithium Corporation of America/Gastonia, NC | 02.68 |
| Binder | Zephyrset K-6544D/Sinclair and Valentine/North Kansas City, MO | 55.56 |

The Yellow Steam Indicator Strips (Run 3) were purchased from Albert Browne, Ltd., Leicester, U.K.

Green Steam Indicator Ink (Run 4) was made by grinding in a ball mill the composition described in Table 1b. The ink was screen printed on Monatec 5111-120 paper and dried.

TABLE 1b

Green Steam Indicator Ink Formulation used in Run 4

| Component | | Weight |
|---|---|---|
| Generic Name | Trade Name/Source/Address | (percent) |
| Copper Carbonate | Sigma-Aldrich Fine Chemicals/St. Louis, Mo. | 32.1 |
| Sulfur | #21-95/Akron Chemical Co./Akron, OH | 08.1 |
| Binder | Zephyrset K-6544D/Sinclair and Valentine/North Kansas City, MO | 59.8 |

Red Steam Indicator Ink (Run 5) was made by milling the composition described in Table 1c. The ink was printed using a Number 20 Meyer bar onto Monatec 5111-120 paper and dried.

TABLE 1c

Red Steam Indicator Ink used in Run 5

| Component | | Weight |
|---|---|---|
| Generic Name | Source, Address | (percent) |
| Nickel dimethylglyoxime | 3M Company, St. Paul, MN | 04.7 |
| Disodium salt of ethylene diamine tetraacetic acid | E. M. Science, Gibbstown, NJ | 19.0 |
| Ethyl Cellulose Binder | Colonial G-20-90-NL/Colonial Printing Ink Co.,/East Rutherford, NJ | 74.3 |
| Ammonium Thiocyanate | Akzo Chemical of America, Chicago, IL | 02.0 |

Two Code 39 bar codes, A and B were prepared from a standard program using a Zebra Stripe Bar Code Printer from Zebra Technologies Corp., Vernon Hills, Ill. Code A is shown schematically in FIG. 1 and Code B is illustrated schematically in FIG. 2. Code A is *123456* and Code B is *123456*7*. Code A can be scanned in either directon to give "123456". Code B can be scanned in either direction to give 7. A combination of Code A and Code B will read "1234567". The ninth bar of *7* was cut out from Code B and scanned with an Intermer 9710 Bar Code Scanner from Intermec Corp., Everitt, Wash. The Code B bar code then read "123456". The strips and sheets which had previously been printed with indicator inks described above for Runs 1–5, but unprocessed, were cut to replace the 9$^{th}$ bar of *7* of Code B. This provided a Modified Code B which read "123456" when scanned. Modified Code Bs were processed for six minutes at 132° C. in the 3013 Amsco Eagle steam sterilizer. In Run 1, the *7* had changed color from off-white to black. When scanned, the Modified and processed Code Bs read "1234567" (Run 1–4). Further results are shown in Table 1d for inks described in Table 1a, Table 1b, the commercially available indicator strips described above, and Table 1c. The number scanned is the number of Modified Code Bs scanned. The Number Read records the number of times the scanned Modified Code B's read "1234567".

TABLE 1d

Scanning Results using Different Steam Indicator Inks and Hues

| | Steam Indicator Ink Hue | | Number Read/ Number Scanned | |
|---|---|---|---|---|
| Run Number | Before | After | Before | After |
| Standard Code B | | | 20/20 | |
| 1 | White | Dark Brown | 0/30 | 28/30 |
| 2 | Off White | Black | 0/30 | 30/30 |
| 3 | Yellow | Purple | 30/30* | 30/30 |
| 4 | Green | Black | 30/30 | 30/30 |
| 5 | Red | White | 0/30 | 0/30 |

*One scanning resulted in a number other than the Standard Code B.

The scanner detected the white to black color changes consistently. Additional indicator ink strips prepared as described for Run 1 were processed at 132° C. in the 3013 Amsco Eagle steam sterilizer for different time intervals to obtain degrees of color change. A Tan color was produced after ½ minute exposure, Brown after 1 minute, Dark Brown after 2 minutes, 1/30 Modified Code Bs read "1234567" for the Tan strips and 10/30 Modified Code Bs read "1234567" for the Brown strips and 28/30 Modified Code Bs Read "1234567" for the Dark Brown strips. Colored filters could be used to detect other color changes which were not read by the scanner used in this example for Runs 3., 4, and 5.

EXAMPLE 2

An indicating composition for use in a hydrogen peroxide sterilization procedure was prepared by combining the elements of the formulation listed in Table 2a.

TABLE 2a

Hydrogen Peroxide Indicator Ink Formulation used in Run 1

| Component | | Weight |
|---|---|---|
| Generic Name | Name/Source/Address | (percent) |
| Acid Fuschin Sodium Salt | Sigma-Aldrich Fine Chemicals/St. Louis, Mo. | 0.18 |
| Rhoplex I-545 | Rohm & Haas Corp./Philadelphia, PA | 36.30 |
| Shellac Bleached Bone Dry | Mantrose Bradshaw Zinsser Group/ Westport, CT | 18.20 |
| Ethyl Alcohol | | 18.20 |
| Isopropyl Alcohol | Exxon Chemical Corp./Houston, TX | 27.22 |

The ink formulation was gravure flood coated onto S&S 410 Grade Filter Paper from Schleicher & Schuell Corp., Keene, N.H. Code 39 bar codes B were modified as described in Example 1. Ten Modified Code Bs were sterilized in a Sterrad 100 from Advanced Sterilization Products (ASP) full cycle and scanned as described in Example 1. The results are shown in Table 2b.

TABLE 2b

Scanning Results

| Run Number | Ink | Hue Before | Hue After | Number Read/Number Scanned Before | Number Read/Number Scanned After |
|---|---|---|---|---|---|
| Standard Code B | | | | 20/20 | |
| 1 | Hydrogen Peroxide Indicator Ink | Dark Purple | White | 0/10 | 9/10 |

An incorrect scan angle can give false results.

EXAMPLE 3

U.S. Pat. Nos. 4,731,222; 4,892,706; 5,037,623; 5,077,008; and 5,091,343 (the entire contents of each of which are herein incorporated by reference) describe liquid peracetic acid sterilization procedures for which the present invention may be employed.

Indicator strips available from Steris Corp., Mentor, Ohio were used to monitor a sterilization process including the use of a liquid peracidic acid solution (e.g. the STERIS SYSTEM I™ AND Steris 20™ Sterilant Concentrate available from Steris Corp.). The ninth bar of Code B was replaced with strips cut from the indicator strips before and after sterilization in the Steris System 1™ Full Processing Cycle. The Modified Code Bs were scanned as described in Example 1.

The results are shown in Table 3a.

TABLE 3a

Scanning Results

| Run Number | Ink | Hue Before | Hue After | Number Read/Number Scanned Before | Number Read/Number Scanned After |
|---|---|---|---|---|---|
| Standard Code B | | | | 20/20 | |
| 1 | Commercial Indicator Strips (Steris) | Dark Purple | Pale Blue | 0/10 | 9/10 |

An incorrect scan angle can give false results.

EXAMPLE 4

"3M™ Comply™ '00311' Dry Heat Indicator Strips" from 3M, St. Paul, Minn. were used to monitor a dry heat process. The ninth bar of Code B was replaced with strips cut from the indicator strips before and after heating in a Tenney Jr. oven for 1 hour at 160° C. The Modified Code Bs were scanned as described in Example 1. The results are shown in Table 4b.

TABLE 4b

Scanning Results

| Run Number | Ink | Hue Before | Hue After | Number Read/Number Scanned Before | Number Read/Number Scanned After |
|---|---|---|---|---|---|
| Standard Code B | | | | 20/20 | |
| 1 | 3M ™ Comply ™ '00311' Dry Heat Indicator Strips | Tan | Black | 2/10 | 10/10 |

EXAMPLE 5

"3M™ Comply™ '00152' Ethylene Oxide Sterilometer Strips" from 3M, St. Paul, Minn. were used to monitor an ethylene oxide sterilization process. The ninth bar of Code B was replaced with strips cut from the indicator strips before and after processing in a 3M 4XL Ethylene Oxide Sterilizer on a full warm cycle. The Modified Code Bs were scanned as described in Example 1. The results are shown in Table 5a.

TABLE 5a

Scanning Results

| Run Number | Ink | Hue Before | Hue After | Number Read/Number Scanned Before | Number Read/Number Scanned After |
|---|---|---|---|---|---|
| Standard Code B | | | | 20/20 | |
| 1 | 3M ™ Comply ™ '00152' EO Sterilometer Strips | Light yellow | Blue | 0/10 | 8/10 |

Colored filters could be used to detect this color change which was difficult to read using this bar code scanner.

EXAMPLE 6

Tests were conducted to determine whether a reading device could accurately read existing, publicly available chemical indicators. Thirty-seven (37) spectral scans were conducted on twenty-two (22) different sterilization indicator strips.

Four different types of sterilization indicator strips were exposed to various levels of sterilants or partial cycles. As shown in FIG. 15, a device was configured on a Newport optical bench from off the shelf instrumentation to spectrally scan the indicator strips. Scanning was done in a photographic quality darkroom to suppress ambient light. The illumination source was Flexilux 250 (endo available from Scholly Fiberoptic GMBH of Denzlingen, West Germany) using an Osram 418 fl quartz halogen lamp (3200 degree K). No filter was used and the optical aperture was fully open. Power was provided to the lamp from 118.9 Volts Alternating Current (VAC) Root Mean Square (RMS) 60 Hertz (HZ). A fiber optic light guide was used to transfer visible light to the indicator strip while blocking infrared (heat). The fiber consisted of a packed smaller glass fiber circular array with 4.78 mm core diameter. No focusing optics were used with the illumination fiber. The illumination source was powered up and allowed to equilibrate for 10 minutes before scanning. Dark field scans were taken before and after scanning the indicator strips to confirm illumination source stability.

The detector was an Ocean Optics S2000 fiber optic spectrometer available from Ocean Optics of Dunedin, Fla. Two quartz fibers (P600-2-SMA) (2 meter in length by 600 micrometers in diameter), a filter holder (FHS-UV), and a collimating lens (74-UV) were used to collect light from the indicator strip. The effective aperture at the plane of the indicator strip was approximately 3 mm in diameter. The spectrometer was connected to a personal computer running the OOI base V1.5 application available from Ocean Optics of Dunedin, Fla. Data was further parsed and charts were generated in Microsoft EXCEL.

Newport positioning devices were used to hold the detection fiber and illumination fiber in fixed geometric relation to the plane of the indicator strip. Illumination incident angle was set at 45 or 90 (FIG. 16) degrees from the plane of the indicator strip. Detector fiber and illumination fibers were 2.5 inches above the plane of the indicator strip. A flat black paper was placed on the optical bench to restrict stray reflections.

Figure 6:
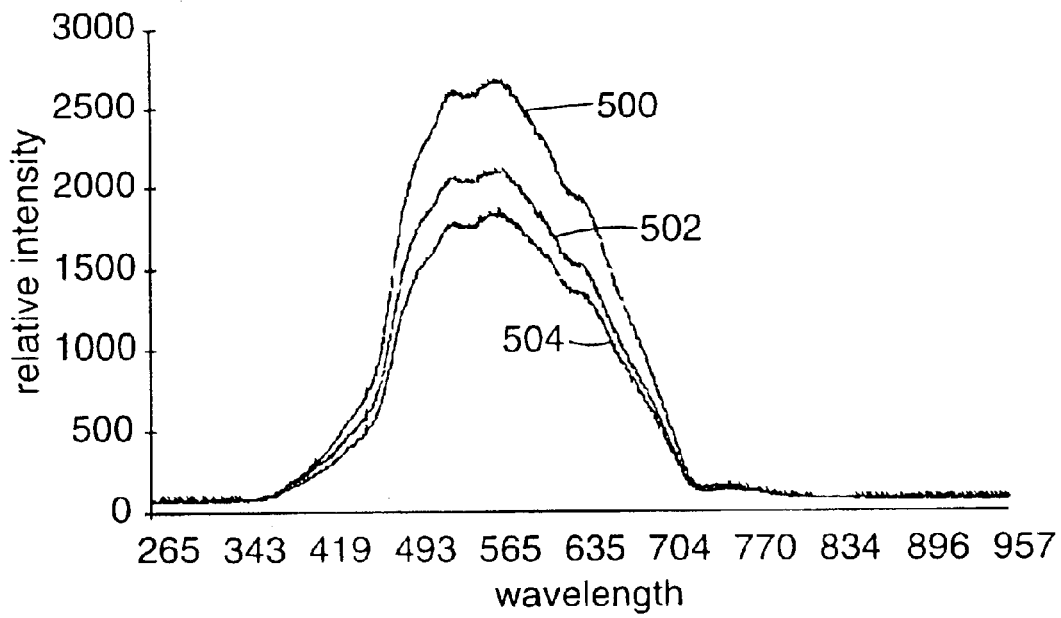
FIG. 6 is a graph showing three spectral scans of sterilization indicators subjected to different degrees of exposure to a sterilization process, which scans were made at a 90 degree illumination incidence angle.

The first set of indicator strips tested was prepared as described in Example for the white steam indicator ink and overcoated with an ultraviolet coating. This chemical indicator is designed to monitor any steam sterilization cycle. It changes from white to dark brown/black after six minutes exposure at 132° C. in the 3013 Amsco Eagle steam sterilizer. FIG. 6 shows three spectral scans made at a 90 degree illumination incidence angle for three white steam indicator strips. After the first steam indicator strip was exposed for six minutes at 132° C. in the 3013 Amsco Eagle steam sterilizer, it appeared black 502 (exposed to sterilant). After a second steam indicator strip was exposed for two minutes at 132° C. in the 3013 Amsco Eagle steam sterilizer, it appeared brown 504 (partial exposure). A third indicator strip was not exposed to any portion of a sterilization cycle and it appeared white 500 (no exposure). These indicator strips had specular first surfaces due to the ultraviolet overcoat.

Figure 7:
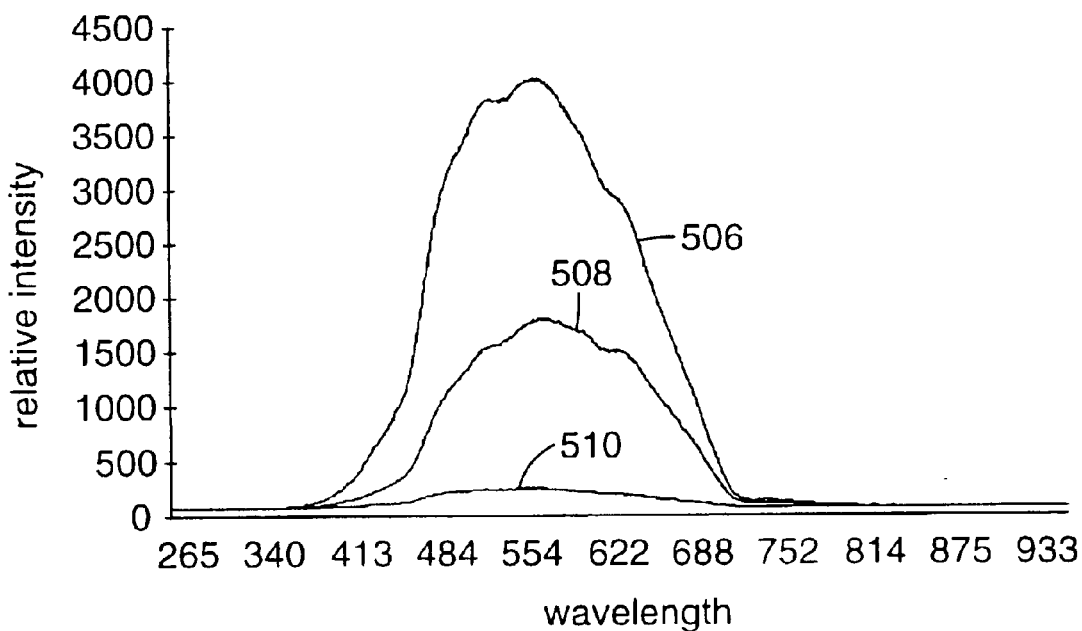
FIG. 7 is a graph showing three spectral scans of the sterilization indicators of FIG. 6, which scans were made at a 45 degree illumination incidence angle.

FIG. 7 shows the scans of the same indicator strips that were used for FIG. 6 but the scans were made at a 45 degree illumination incidence angle. Reference character 510 represents black (exposed to sterilant), character 508 brown (partial exposure), and character 506 white (no exposure). Note the improved differences in relative intensity for the contrast changes.

The second set of indicator strips was "3M™ Comply™ '00152' EO Chemical Indicator Strip". This indicator strip is designed to monitor the ethylene oxide (EO) sterilization process. It changes from yellow to blue when exposed in a 3M™ StenVace™ 4XL Ethylene Oxide Sterilizer on a full warm cycle.

Figure 8:
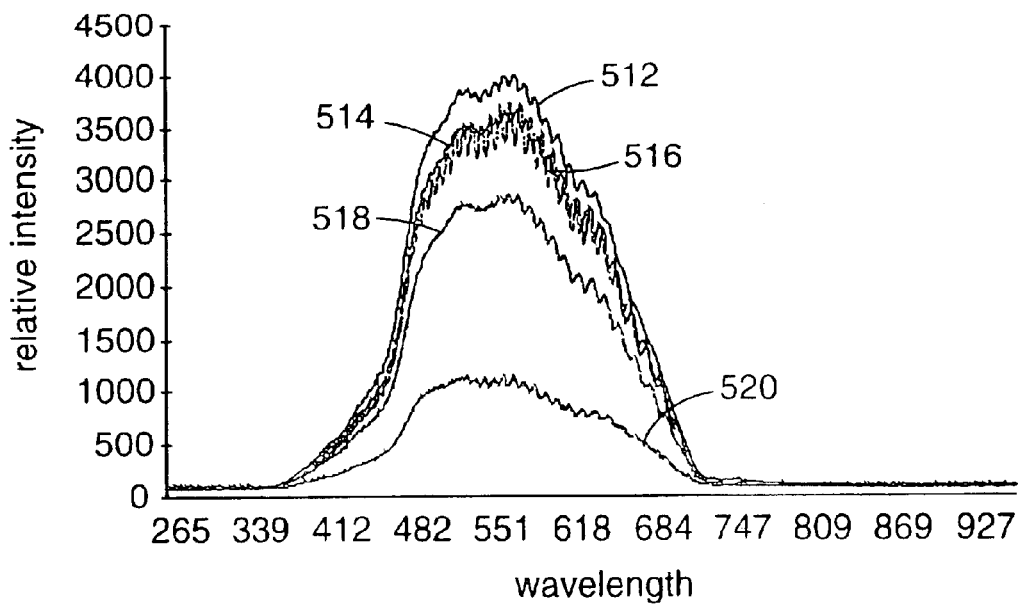
FIG. 8 is a graph showing five spectral scans of sterilization indicators subjected to different degrees of exposure to a sterilization process, which scans were made at a 90 degree illumination incidence angle.

FIG. 8 shows spectral scans made at a 90 degree illumination incidence angle for five EO chemical indicator strips. After two EO indicator strips were exposed for a full warm EO cycle, they appeared blue 512, 520 (fully exposed to sterilant). After a third EO indicator strip was exposed for 10 minutes, it appeared yellow/green 514 (partial exposure). After a fourth EO indicator strip was exposed for 30 minutes, it appeared green 518 (more exposure). A fifth EO indicator strip was not exposed to any portion of a sterilization cycle and it appeared yellow 516 (no exposure). These indicator strips also had specular first surfaces due to a plastic lamination to prevent the surface of the ink from coming in contact with items being sterilized. Note the variability for reading of the two blue indicator strips 512, 520 in FIG. 8 which were fully exposed to sterilant; and therefore, should be similar to each other if not the same.

Figure 9:
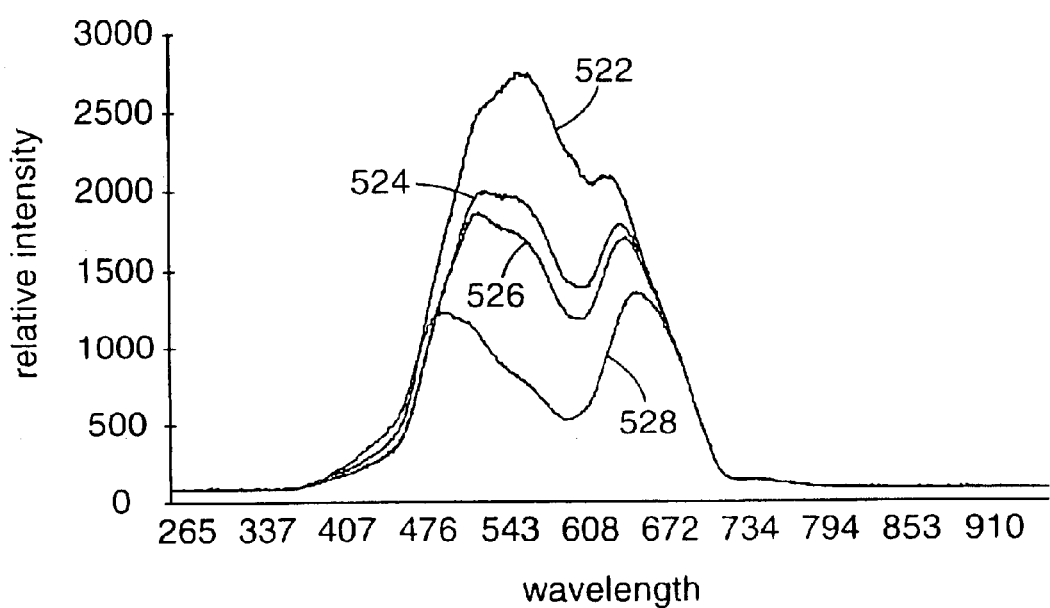
FIG. 9 is a graph showing four spectral scans of the sterilization indicators of FIG. 8, which scans were made at a 45 degree illumination incidence angle.

FIG. 9 shows scans of the same indicator strips made at a 45 degree illumination incidence angle. They appeared blue 528 (exposed to sterilant), yellow/green 524 (partial exposure), green 526 (less exposure), yellow 522 (no exposure). Note the improved spectral discrimination.

The third set of indicator strips was "3M™ Comply™ EO Chemical Indicator Strip", Model 1251. This indicator strip is designed to monitor the ethylene oxide (EO) sterilization process. It changes from red to green when exposed in a 3M™ SteriVac™ 4XL Ethylene Oxide Sterilizer on a full warm cycle.

Figure 10:
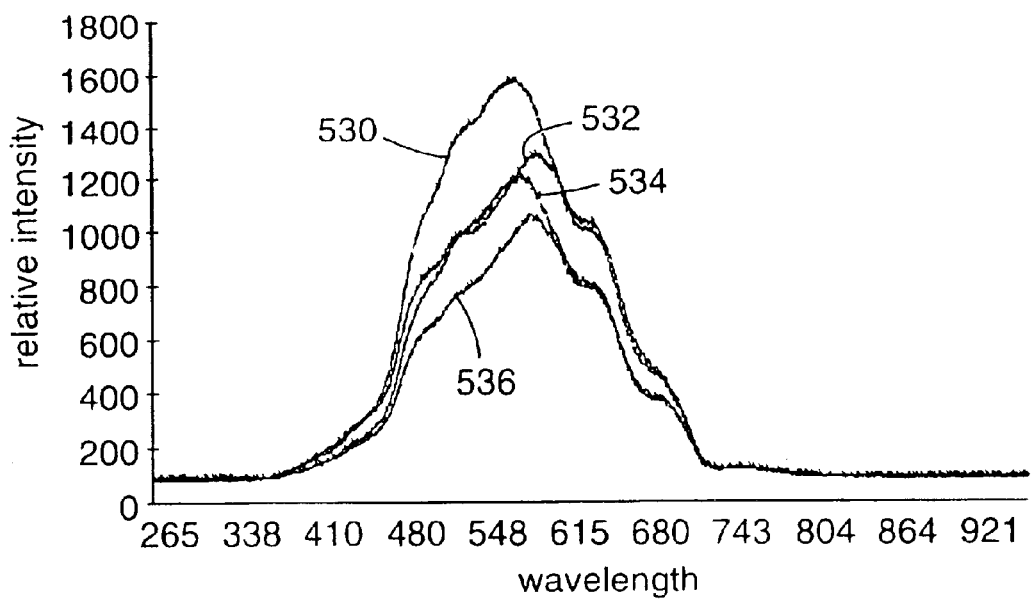
FIG. 10 is a graph showing four spectral scans of sterilization indicators subjected to different degrees of exposure to a sterilization process, which scans were made at a 90 degree illumination incidence angle.

FIG. 10 shows spectral scans made at a 90 degree illumination incidence angle for four model 1251 I EO indicator strips. After a first EO indicator strip was exposed for 60 minutes at 50% relative humidity (RH), it appeared green 530 (exposed to sterilant). After a second EO indicator strip was exposed for 30 minutes at 90% RH, it appeared olive 534 (partial exposure). After a third EO indicator strip was exposed for 21 minutes at 30% RH, it appeared brown 536 (less exposure). A fourth EO indicator strip was not exposed to any portion of a sterilization cycle and it appeared red 532 (no exposure). These indicator strips had specular first surfaces made by covering the exposed ink with clear "Scotch™ Mailing Tape".

Figure 11:
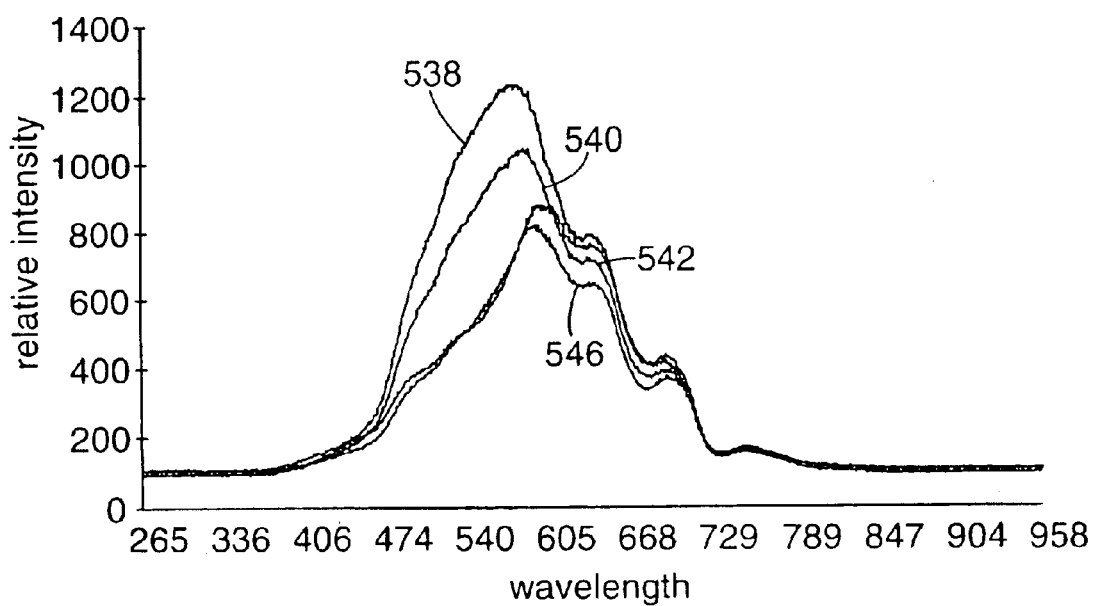
FIG. 11 is a graph showing four spectral scans of the sterilization indicators of FIG. 10, which scans were made at a 45 degree illumination incidence angle.

FIG. 11 shows scans of the same EO indicator strips of FIG. 10 but made at a 45 degree illumination incidence angle. They appeared green 538 (exposed to sterilant), olive 540 (partial exposure), brown 546 (less exposure), and red 542 (little exposure). Note the improved spectral discrimination. The olive and red indicator strips have curves that are very similar in shape as well as intensity when scanned using a 90 degree illumination incidence angle (FIG. 10). In contrast, the curves for the same two indicator strips have quite apparent differences when scanned using a 45 degree illumination incidence angle especially at wavelengths of between 500 and 550 nanometers (FIG. 11).

The fourth set of indicator strips were the same as the indicator strips used for FIG. 10 and FIG. 11 except the ink was not covered or coated. The first surfaces are diffuse not specular.

Figure 12:
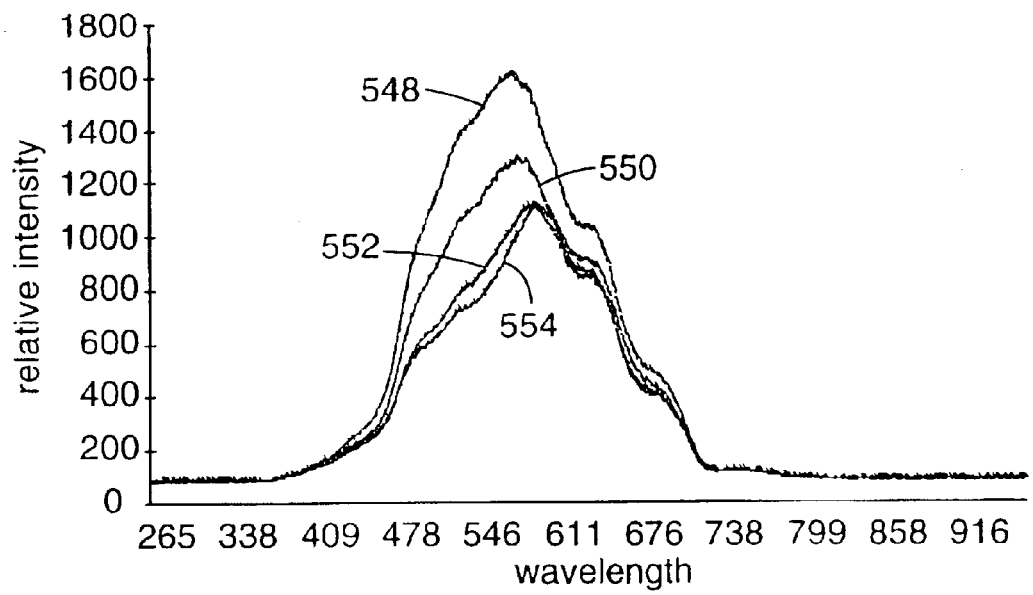
FIG. 12 is a graph showing four spectral scans of sterilization indicators subjected to different degrees of exposure to a sterilization process, which scans were made at a 90 degree illumination incidence angle.

FIG. 12 shows spectral scans made at a 90 degree illumination incidence angle for four Model 1251 I EO indictor strips. After a first EO indicator strip was exposed for 60 minutes at 50% relative humidity (RH), it appeared green 548 (exposed to sterilant). After a second EO indicator strip was exposed for 30 minutes at 90% RH, it appeared olive 550 (partial exposure). After a third EO indicator strip was exposed for 21 minutes at 30% RH, it appeared brown 552 (less exposure). A fourth EO indicator strip was not exposed to any portion of a sterilization cycle and it appeared red 554 (no exposure).

Figure 13:
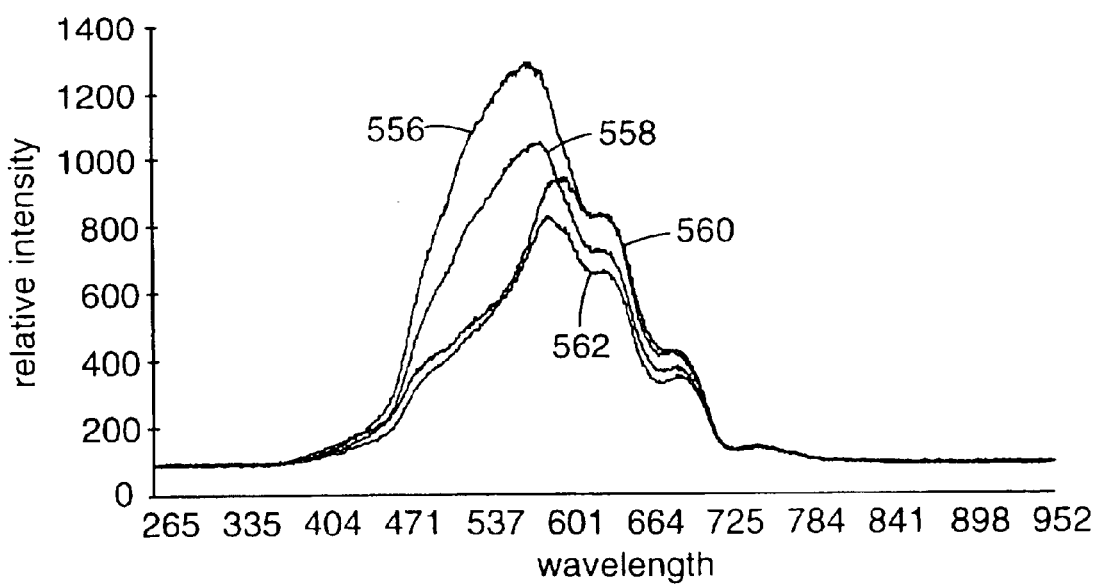
FIG. 13 is a graph showing four spectral scans of the sterilization indicators of FIG. 12, which scans were made at a 45 degree illumination incidence angle.

FIG. 13 shows scans of the same EO indicator strips of FIG. 12, but made at a 45 degree illumination incidence angle. They appeared green 556 (exposed to sterilant), olive 558 (partial exposure), brown 562 (less exposure), and red 560 (no exposure). Note the improved spectral discrimination.

This example shows that specular first surface indicator strips measured at a 90 degree illumination incidence angle were sensitive to flatness and geometric position. Preferable geometry for a reader of these existing sterilization indicators would include detection normal to the plane of the indicator strip and illumination at a 45 degree incidence angle to the plane of the indicator strip.

Readers

Referring now to FIGS. 7 and 19 and example 6, there is shown a method of determining whether the sterilization indicator has been subjected to an adequate sterilization process. Curves for the various sterilization cycles are shown in FIG. 7. Curve 510 was generated from a sterilization indicator that was subjected to an adequate sterilization process. Curves 506 and 508 wer generated from sterilization indicators that were subjected to inadequate sterilization processes.

A suitable range of wavelengths may be selected. For example, in FIG. 19, the range is between 493 and 635. A maximum intensity may then be selected by, for example, obtaining intensity information from sterilization indicators subjected to a sterilization cycle known to be adequate. In this example, the intensity selected is 500.

The reader can then read the sterilization indicator, compare the read intensity with the selected maximum and determine whether it exceeds the maximum. The determination of whether the sterilization cycle was adequate (fully processed or not fully processed) may then be made as shown in FIG. 19.

EXAMPLE 7

This example demonstrates a method and formulation for placing a chemical indicator ink into a desk jet printing cartridge. Inkjet printing technology is described in U.S. Pat. Nos. 4,872,026; 4,907,018; 5,594,483 and 5,874,978 (the entire contents of which are herein incorporated by reference). An ink jet printed sterilization indicator allows the user to print her/his own name, identification, or pattern onto the label of something being processed in a specific chemical environment. By placing several inks into these cartridges, one creates a manufacturing process whereby different inks can alternately be placed on a web, depending on the production demand. This would allow one (preferably an automated) assembly line, with many outputs, to replace several existing lines. FIG. 14 is a perspective view of a representative ink jet printer cartridge 100 designed to hold three different indicator ink chemistries in compartments 102, 104, and 106. The compartments are covered so that the inks cannot leak or mix between compartments.

A vapor hydrogen peroxide/plasma chemical indicator was prepared by using the composition shown in Table 7a and Table 7b.

TABLE 7a

Sterrad Indicator Ink Composition

| Component | | Weight |
|---|---|---|
| Generic Name | Trade Name/Source/Address | (grams) |
| Acid Fuchsin Sodium Salt | Sigma-Aldrich Fine Chemicals, St. Louis, MO | 2.5 |
| Deionized water | | 50 |
| Polyethylene glycol 200 | Exxon Chemical Company, Houston, TX | 20 |

TABLE 7b

Sterrad Indicator Ink Composition

| Component | | Weight |
|---|---|---|
| Generic Name | Trade Name/Source/Address | (grams) |
| Acid Fuchsin Sodium Salt | Sigma-Aldrich Fine Chemicals | 2.5 |
| Water soluble green dye | DB-892 Colorcon, West Point, PA | 0.6 |
| Deionized water | | 50 |
| Ethylene glycol | Sigma-Aldrich Fine Chemicals | 10 |
| Diethylene glycol | Sigma-Aldrich Fine Chemicals | 10 |

The composition was prepared by mixing the components of the composition together in a 16 ounce bottle on a paint mixer until the solid particles were dissolved. The composition was then filtered through Whatman # 4 filter paper from Whatman, Inc., Clifton, N.J. to remove the particle sizes greater than 20–25 micrometers which might clog an ink jet cartridge. Next the compositions were placed in an ink jet cartridge for a Hewlett Packard (HP) desktop printer and were printed on a 216 by 279 mm, white, 75 grams per square meter, sheet of Cascade™ X-9000 copy paper from Boise Cascade Paper Division, Boise Id. using PowerPoint software from Microsoft, Redmond, Wash. These were then "laminated" front and back with Scotch™ Magic™ tape.

Figure 5:
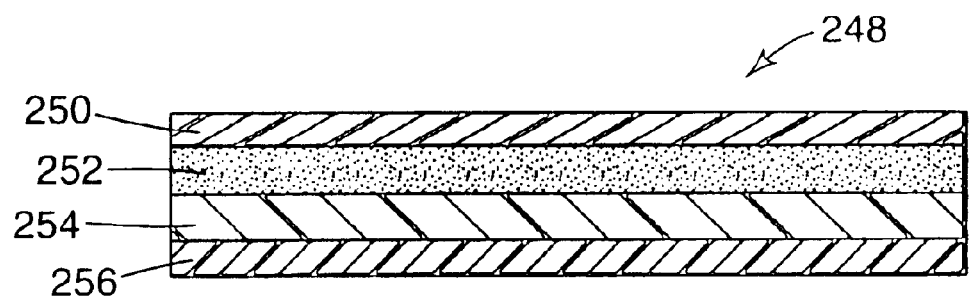
FIG. 5 is a schematic side view of one embodiment of a construction of a sterilization indicator according to one aspect of the present invention.

The composition described in Table 7a was also printed on polyester film with a polyvinylidene chloride (PVDC) coating available as 3M Transparency Film CG3460 from 3M Company, St. Paul, Minn. Referring to FIG. 5, indicator ink 254 was printed on polyester film 256 using PowerPoint. The indicator ink was covered with a lamination of an adhesive layer 252 and a film layer 250. The adhesive layer 252 was prepared using an isooctyl acrylate/acrylamide adhesive binder and an isooctyl acrylate/acrylic acid (IOA/AA) copolymer microsphere system as described in PCT publication no. 94/194420 or its priority document U.S. patent application Ser. No. 08/018,927, filed Feb. 16, 1993, entitled, "System Comprising Release Agent and High Peel Adhesion Repositionable Adhesive" by L. Bilski, R. Kumar, T. Mertens, and S. Wilson (the entire contents of which are herein incorporated by reference). The film layer 250 was a 2.5 mil polyester film that is transparent and has good heat stability coated with a primer to aid in bonding of the adhesive to the backing.

When exposed to a standard Sterrad 100 Hospital cycle (44 minutes of hydrogen peroxide diffusion) and when exposed for shorter period of times such as 23 and 36 minutes, the above constructions demonstrated their ability to perform as moving front indicators. The hydrogen peroxide diffuses either through the paper as in the case of the indicator ink printed paper sandwiched between two films or through the microsphere/binder adhesive 252 as in the case of the indicator ink covered by IOA/AA microspheres and adhesive binder. The moving front progresses toward the center of the device as it is exposed for longer periods of time. The paper substrate used could be varied (other cellulosics, perhaps nonwovens) depending on the environment of exposure or the production demands. The adhesive used could be any microsphere adhesive which would allow the diffusion of hydrogen peroxide such as those described in U.S. Pat. Nos. 3,691,140; 4,166,152,4,049,483; 4,855,170 and 3,857,731. If neither the backing 256 for the indicator ink chemistry or the adhesive layer 252 are permeable to the sterilant, then the indicator ink chemistry should be exposed directly to the sterilant.

Another advantage of using the ink jet cartridge is that the ink is printed in very small dots of color (600 dpi in this example). This aids the observer's ability to see the location of the front since the movement of the peroxide either reacts with a given dot or not leaving a clearly defined line between the green (reacted) and purple (unreacted) hues.

On the individual user basis, the ink jet cartridge allows a user to print their own indicator patterns and identification. It also provides more labeling options (ID trays, etc. on labels). For example, the information provided on the label 410 in FIG. 30 could be modified according to the desires of the users, not the manufacturers.

Several different types of sterilization indicator processes could be used. A large variety of inks, timings, substrates, etc. could be placed on one large assembly line. This would allow greater versatility, lower cost, fewer operators, and greater precision in the plant.

Readers

EXAMPLE 7

The chemical indicator described in Table 7a visually changes from purple to green when exposed to a vapor hydrogen peroxide plasma phase for a certain amount of time and at a certain concentration of hydrogen peroxide. Along with this visual change, a corresponding change in the wavelength at which the indicator absorbs light can also be detected. A chromaticity diagram shows that this corresponds to an initial primary absorbance at approximately $\lambda_0=460$ nm (unexposed) and a final absorbance at approximately $\lambda_1=495$ nm (fully exposed).

The processor of a reader or scanner for this chemical indicator may be programmed such that the initial (unexposed) indicator's primary absorbtion relative intensity is set to 100%. As the individual molecules of the indicator chemistry react they will begin to absorb at a different wavelength ($\lambda_1$). As the sterilization cycle proceeds, there will be a decrease in the relative intensity (from $RI_{0,\,init}$ to $RI_{0,\,final}$) of $\lambda_0$ and an increase in relative intensity (from $RI_{1,\,init}$ to $RI_{1,\,final}$) of $\lambda_1$.

Alternatively, other algorithms could be utilized to enable the reader to automatically evaluate the indicator and determine if adequate sterilization conditions occurred.

In a first embodiment, the processor may be programmed to respond to the remaining relative intensity of $\lambda_0$. This threshold value (a) (see equation below) should correspond to a suitable decrease in the initial color to represent an "accept" cycle of the sterilizer. That is:

$$\text{IF } \left( \frac{RI_{0,initial} - RI_{0,final}}{RI_{0,initial}} \right) \leq a, \text{ THEN "ACCEPT" or "ADEQUATE"}$$

$$\text{IF } \left( \frac{RI_{0,initial} - RI_{0,final}}{RI_{0,initial}} \right) > a, \text{ THEN "REJECT" or "INADEQUATE"}$$

In a second embodiment, the processor may be programmed to respond to the increase of relative intensity of $\lambda_1$. The threshold value (b) (see equation below) should correspond to a suitable increase in the final color to represent an "accept" cycle of the sterilizer. That is:

$$\text{IF } \left( \frac{RI_{1,final} - RI_{1,initial}}{RI_{1,final}} \right) \leq b, \text{ THEN "ACCEPT" or "ADEQUATE"}$$

$$\text{IF } \left( \frac{RI_{1,final} - RI_{1,initial}}{RI_{1,final}} \right) > b, \text{ THEN "REJECT" or "INADEQUATE"}$$

In yet another embodiment, a combination of the two factors can be implemented:

$$\left( \text{IF } \left( \frac{RI_{0,initial} - RI_{0,final}}{RI_{0,initial}} \right) \leq a \right) \text{ AND } \left( \text{IF } \left( \frac{RI_{1,final} - RI_{1,initial}}{RI_{1,final}} \right) \leq b \right),$$
$$\text{THEN "ACCEPT" or "ADEQUATE"}$$

$$\left( \text{IF } \left( \frac{RI_{0,initial} - RI_{0,final}}{RI_{0,initial}} \right) > a \right) \text{ OR } \left( \text{IF } \left( \frac{RI_{1,final} - RI_{1,initial}}{RI_{1,final}} \right) > b \right),$$
$$\text{THEN "REJECT" or "INADEQUATE"}$$

Yet another embodiment includes the step of integrating the relative intensities over a range of wavelengths surrounding the initial and final colors instead of using two discrete wavelength values. Other mathematical correlations of these parameters could be used to maximize sensitivity and increase the safety margin.

The threshold values (a) and (b) can be arrived at by using information taken from reference indicators subjected to a sterilization cycle known to be adequate or marginally adequate.

By implementing an algorithm that is based on the percentage of a discrete or range of wavelengths, it is possible to include the option of a self-calibrating reader. This is made possible both by means of the earlier algorithms, which use relative changes instead of absolute changes in relative intensities, and by means of appropriate logic programming and memory. The self-calibrating reader would initially read the indicator absorbance over the band of the visible spectrum. By logic circuitry, the reader would establish its own baseline and determine the wavelength, or range thereof, that has the greatest absorbance. From a group of spectra stored in its reference memory, it could be programmed to determine which type of sterilization indicator it was viewing (e.g. a steam chemical indicator, an ethylene oxide chemical indicator or models thereof). For instance, if the reader found that the maximum absorbance of the chemical indicator was in the range of 760 nm, the reader itself would be able to determine that this represents a certain purple indicator that is sensitive to hydrogen peroxide. The reader can also read from memory that this indicator should finally achieve a spectrum that shows an absorbance at 495 nm—along with a value of relative change of both relative intensities.

If a color standard were also employed, the reader could determine its own life cycle. That is, as it notes that a relative intensity for the standard has shifted (due to bulb fatigue, scratches on optics, weak battery, etc.), it can make the corresponding shifts in its logic to compensate for the changes. If the memory contained spectra of multiple stages of each sterilization cycle, it would also be able to establish which parameters have not been met. Additionally, it may also be able to quantify how far from adequate the parameters are as well.

The present invention has now been described with reference to several embodiments and examples thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

What is claimed is:

1. A system comprising:
   (A) A chemical indicator comprising a substantially flat surface capable of reflecting energy therefrom, and a sterilizing agent sensitive ink associated with the surface, the ink providing a first indicating state prior to being exposed to the sterilization process, and a second indicating state after being exposed to at least a portion of the sterilization process, the first and the second indicating states being distinguished one from the other by color of the surface; and
   (B) An apparatus for reading the chemical indicator, the apparatus comprising;
      (i) an illumination source configured and positioned to provide energy and to direct the energy toward the substantially flat surface of the chemical indicator;
      (ii) a detector configured to collect energy reflected from the substantially flat surface and to provide a signal characteristic of the wavelength of the energy reflected from the substantially flat surface;

(iii) positioning means for positioning the substantially flat surface of the chemical indicator relative to the illumination source and the detector;

(iv) a controlled controllably connected to the detector and the illumination source; and (v) processing means for processing the signal from the detector to distinguish the first and second states and for determining whether the chemical indicator is in the first state or the second state, the processing means including nonvolatile memory that includes reference data comprising data generated from sterilization indicators that have been exposed to varying degrees of a sterilization process.

2. An apparatus according to claim 1 wherein the illumination source is capable of providing light at an angle of incidence with the surface of more than approximately ten degrees and less than ninety degrees.

3. An apparatus according to claim 2 wherein the detector collects light from the surface at a substantially normal angle.

4. An apparatus according to claim 1 wherein the illumination source is capable of scanning through a variety of wavelengths of light.

5. An apparatus according to claim 1 wherein the illumination source comprises a plurality of light sources capable of providing different wavelengths of light and an optical mixer.

6. An apparatus according to claim 1 wherein the detector is sensitive in a substantially repeatable fashion to a variety of light sources.

7. An apparatus according to claim 1 wherein the processing means includes means for comparing information generated from said chemical indicator with reference data.

8. An apparatus according to claim 1 wherein the processing means includes means for calibrating components of the apparatus.

9. An apparatus according to claim 1 further comprising means for reading at least a portion of a bar code printed from a permanent, substantially colorfast ink.

10. An apparatus according to claim 1 further including output means for communicating the results of the chemical indicator to a user or another computer.

11. An apparatus according to claim 1 wherein the chemical indicator comprises a code comprising a portion including a permanent, substantially colorfast ink and a portion comprising a sterilization process sensitive ink, the code having a spatial size and position, and the apparatus comprises a linear charge coupled device (CCD) capable of detecting the spatial size and position of said code.

12. An apparatus according to claim 1 wherein the positioning means includes a means for holding the chemical indicator in a fixed, predetermined orientation relative to said illumination source and said detector.

13. An apparatus according to claim 1 wherein the processing means comprises a complementary metal oxide semiconductor (CMOS) circuit.

14. An apparatus according to claim 1 wherein the processing means comprises a programmable microprocessor.

15. An apparatus according to claim 1 wherein the processing means includes memory means for storing sterilization information.

16. An apparatus according to claim 1 wherein the processing means includes control means.

* * * * *

UNITED STATES PATENT AND TRADEMARK OFFICE
CERTIFICATE OF CORRECTION

PATENT NO. : 6,884,394 B1
DATED : April 26, 2005
INVENTOR(S) : Hehenberger, Rodney K.

It is certified that error appears in the above-identified patent and that said Letters Patent is hereby corrected as shown below:

Column 1,
Line 48, delete "health" and insert -- Health --, therefore;

Column 7,
Line 36, after "4,643,876" delete "," and insert -- ; --, therefore;
Line 45, insert -- 25 -- before the word "could";

Column 8,
Line 46, delete "et al," and insert -- et al. --, therefore;

Column 13,
Line 59, delete "(I's)" and insert -- (1's) --, therefore;

Column 14,
Lines 3 and 62, delete "1996)" and insert -- (1996) --, therefore;
Line 25, delete "(+31-0" and insert -- (+3/-0 --, therefore;

Column 18,
Line 29, after the word "data" insert -- . --;

Column 22,
Line 4, after "(FIG. 3)" delete ".";

Column 27,
Line 45, delete "directon" and insert -- direction -- therefore;

Column 31,
Line 21, insert -- 1 -- before the word "for";
Line 50, delete "Sten Vace$^{TM}$" and insert -- Steri Vac$^{TM}$ --, therefore;

Column 32,
Lines 13 and 41, after "1251" delete "I";

Column 33,
Line 4, delete "wer" and insert -- were --, therefore;

Column 34,
Line 9, delete "Id." and insert -- ID --, therefor;

UNITED STATES PATENT AND TRADEMARK OFFICE
CERTIFICATE OF CORRECTION

PATENT NO.    : 6,884,394 B1
DATED         : April 26, 2005
INVENTOR(S)   : Hehenberger, Rodney K.

It is certified that error appears in the above-identified patent and that said Letters Patent is hereby corrected as shown below:

Column 37,
Line 4, delete "controlled" and insert -- controller --, therefore;

Column 38,
Line 15, after "position" delete "," and insert -- ; --, therefore.

Signed and Sealed this

Twenty-third Day of August, 2005

JON W. DUDAS
*Director of the United States Patent and Trademark Office*